United States Patent
Duan

(10) Patent No.: US 6,495,548 B1
(45) Date of Patent: Dec. 17, 2002

(54) LACTAM INHIBITORS OF MATRIX METALLOPROTEINASES, TNF-α AND AGGRECANASE

(75) Inventor: Jingwu Duan, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/540,056

(22) Filed: Mar. 31, 2000

Related U.S. Application Data

(60) Provisional application No. 60/127,594, filed on Apr. 2, 1999.

(51) Int. Cl.[7] ............... C07D 215/38; C07D 263/04; C07D 263/16; C07D 207/12; C07D 207/24
(52) U.S. Cl. ............... 514/231.5; 514/314; 514/374; 514/422; 514/424; 544/128; 546/175; 548/229; 548/543
(58) Field of Search ............... 546/175; 548/543, 548/229; 514/231.5, 314, 374, 422, 424; 544/128

(56) References Cited

U.S. PATENT DOCUMENTS 5,773,610 A * 6/1998 McWhorter et al. ........ 540/200

FOREIGN PATENT DOCUMENTS

| EP | 0200425 | 12/1986 |
|---|---|---|
| EP | 0574758 | 12/1993 |
| GB | 2268934 | 1/1994 |
| WO | 9422820 | 10/1994 |
| WO | 9424140 | 10/1994 |
| WO | 9509841 | 4/1995 |
| WO | 9533719 | 12/1995 |
| WO | 9732846 | 9/1997 |
| WO | 9736900 | 10/1997 |
| WO | 9909000 | 2/1999 |
| WO | 9918074 | 4/1999 |

OTHER PUBLICATIONS

Nishio et al. (J. Chem. Soc., Perkin Trans. 1 (1996), (9), 921–926) Abstract.*
Abstract of WO 97/32846.*
Abstract of WO 97/36900 (1997).*
Abstract of WO 95/33719 (1995).*
Abstract of WO 94/22820 (1994).*
Abstract; Horii et al. (J. Antibiot. (1985), 38(3), 302–11).*
Chemical Abstracts, vol. 96, No. 3, Jan. 8, 1982, Columbus, Ohio, U.S., Abstract No. 162694, Das et al. "Pharmacologically active substituted thiazolidinediones" XP002143299 & IN–A–148064 abstract.
Chemical Abstracts, vol. 87, No. 1, Jul. 4, 1977, Columbus, Ohio, U.S., Abstract No. 218, Korohoda et al. "Synthesis of 3–aryl–2–thiohydantoin– and 3–arylhydantoin–5–acetic acids . . . " XP002143300 & Pol. J. Pharmacol. Pharm. 1976 28 (5), 423–427 abstract.

* cited by examiner

*Primary Examiner*—Bruck Kifle
(74) *Attorney, Agent, or Firm*—David H. Vance

(57) ABSTRACT

The present application describes novel lactams and derivatives thereof of formula I:

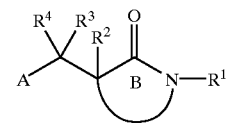

or pharmaceutically acceptable salt forms thereof, wherein ring B is a 4–8 membered lactam containing from 0–3 additional heteroatoms selected from N, O, and S, which are useful as inhibitors of matrix metalloproteinases, TNF-α, and aggrecanase.

20 Claims, No Drawings

LACTAM INHIBITORS OF MATRIX METALLOPROTEINASES, TNF-α AND AGGRECANASE

This application claims the benefit of Provisional Application No. 60/127,594, filed Apr. 2, 1999.

FIELD OF THE INVENTION

This invention relates generally to novel lactam inhibitors of matrix metalloproteinases, TNF-α, and aggrecanase, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumsatnces including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-α from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechansisms are involved.

There are several patents which disclose hydroxamate and carboxylate based MMP inhibitors.

WO95/09841 describes compounds that are hydroxamic acid derivatives and are inhibitors of cytokine production.

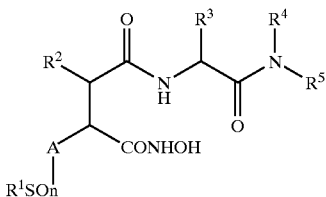

EP 574,758 A1 illustrates hydroxamic acid derivatives as collagenase inhibitors having the general formula:

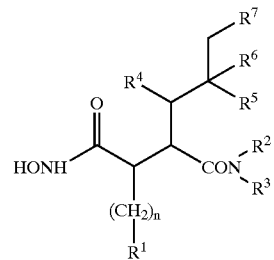

GB 2 268 934 A and WO 94/24140 claim hydroxamate inhibitors of MMPs as inhibitors of TNF production.

WO 97/32846 depicts hydroxamic acid derivatives as MMP inhibitors having the general formula:

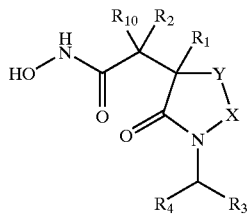

wherein X and Y are carbon or nitrogen, and $R_3$ and $R_4$ can be a variety of groups including amides, aryls, heterocycles and cycloalkyls. Compounds of this sort are not considered to be part of the present invention.

The compounds of the current invention act as inhibitors of MMPs, aggrecanase and/or TNF. These novel molecules are provided as anti-inflammatory compounds and cartilage protecting therapeutics. The inhibiton of aggrecanase, TNF-C, and other metalloproteinases by molecules of the present invention indicates they are anti-inflammatory and should prevent the degradation of cartilage by these enzymes, thereby alleviating the pathological conditions of osteo- and rheumatoid arthritis.

SUMMARY OF THE INVENTION

Accordingly, one object of the present invention is to provide novel lactams which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

It is another object of the present invention to provide novel lactams for use in therapy.

It is another object of the present invention to provide the use of novel lactams for the manufacture of a medicament for the treatment of an inflammatory disorder.

It is another object of the present invention to provide the use of novel lactams for the manufacture of a medicament for the treatment of a condition or disease mediated by MMPs, TNF, aggrecanase, or a combination thereof.

These and other objects, which will become apparent during the following detailed description, have been achieved by the inventors' discovery that compounds of formula (I):

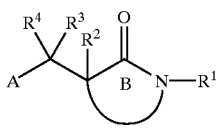

I or pharmaceutically acceptable salt or prodrug forms thereof, wherein A, B, $R^1$, $R^2$, $R^3$, and $R^4$ are defined below, are effective metalloprotease inhibitors.

DETAILED DESCRIPTION OF PREFERRED EMBODIMENTS

[1] Thus, in an embodiment, the present invention provides a novel compound of formula I:

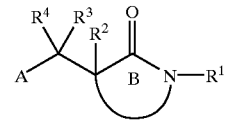

I or a stereoisomer or pharmaceutically acceptable salt form thereof, wherein;

A is selected from $COR^5$, $-CO_2H$, $C(RR')CO_2H$, $-CO_2R^6$, $-CONHOH$, $-C(RR')CONHOH$, $-CONHOR^5$, $-CONHOR^6$, $-NHR^a$, $-N(OH)C(O)R^5$, $-SH$, $-CH_2SH$, $-SONHR^a$, $SN_2H_2R^a$, $PO(OH)_2$, and $PO(OH)NHR^a$;

ring B is a 4–8 membered cyclic amide containing from 0–3 additional heteroatoms selected from O, $NR^a$, and $S(O)_p$, 0–1 additional carbonyl groups and 0–1 double bonds;

$R^1$ is $U-X-Y-Z-U^a-X^a-Y^a-X^b-Z^a$;

U is absent or is selected from: $NR^a$, $C(O)$, $C(O)O$, $C(O)NR^a$, $NR^aC(O)$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-10}$ alkylene, $C_{2-10}$ alkenylene, and $C_{2-10}$ alkynylene;

Y is absent or selected from O, $NR^a$, $S(O)_p$, and $C(O)$;

Z is absent or selected from a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$U^a$ is absent or is selected from: O, $NR^a$, $C(O)$, $C(O)O$, $OC(O)$, $C(O)NR^a$, $NR^aC(O)$, $OC(O)O$, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

$X^a$ is absent or selected from $C_{1-10}$ alkylene, $C_{2-10}$ alkenylene, $C_{2-10}$ alkynylene;

$Y^a$ is absent or selected from O, $NR^a$, $S(O)_p$, and $C(O)$;

$X^b$ is absent or selected from $C_{1-10}$ alkylene, $C_{2-10}$ alkenylene, $C_{2-10}$ alkynylene;

$Z^a$ is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

provided that:
(a) when U is absent, X and Y are absent; and,
(b) $R^1$ is other than unsubstituted alkyl, alkylene-Z, alkylene-$Z^a$, alkylene-amino-Z, alkylene-amino-$Z^a$, alkylene-amino-Z-$Z^a$, and alkylene-amino-Z-alkylene-$Z^a$;

$R^2$ is selected from H, Q', $C_{1-10}$ alkylene-Q', $C_{2-10}$ alkenylene-Q', $C_{2-10}$ alkynylene-Q', $(CRR')_rO(CRR')_r-Q'$, $(CRR')_rNR^a(CRR')_r-Q'$, $(CRR')_rNR^aC(O)(CRR')_r-Q'$, $(CRR')_rC(O)NR^a(CRR')_r-Q'$, $(CRR')_r C(O)(CRR')_r-Q'$, $(CRR')_rC(O)O(CRR')_r-Q'$, $(CRR')_rS(O)_p(CRR')_r-Q'$, $(CRR')_rSO_2NR^a(CRR')_r-Q'$, $(CRR')_rNR^aC(O)NR^a(CRR')_r-Q'$, $(CRR')_rOC(O)NR^a(CRR')_r-Q'$, and $(CRR')_rNR^aC(O)O(CRR')_r-Q'$;

R, at each occurrence, is independently selected from H, $CH_3$, $CH_2CH_3$, $CH(CH_3)_2$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

Q' is selected from H, a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$R^3$ is selected from H, Q, $C_{1-10}$ alkylene-Q, $C_{2-10}$ alkenylene-Q, $C_{2-10}$ alkynylene-Q, $(CRR')_rO(CRR')_r$—Q, $(CRR')_rNR^a(CRR')_r$—Q, $(CRR')_rC(O)(CRR')_r$—Q, $(CRR')_rC(O)O(CRR')_r$—Q, $(CRR')_rOC(O)(CRR')_r$—Q, $(CRR')_rC(O)NR^a(CRR')_r$—Q, $(CRR')_rNR^aC(O)(CRR')_r$—Q, $(CRR')_rOC(O)O(CRR')_r$—Q, $(CRR')_rOC(O)NR^a(CRR')_r$—Q, $(CRR')_rNR^aC(O)O(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a(CRR')_r$—Q, $(CRR')_rNR^aC(O)(CRR')_r$"NHQ, $(CRR')_rNR^aC(O)(CRR')_rNHC(O)OR^a$, and $(CRR')_rNR^aC(O)(CRR')_rNHC(O)(CRR')_rNHC(O)OR^a$, Q is selected from H, a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$R^4$ is selected from H, $C_{1-10}$ alkylene-H, $C_{2-10}$ alkenylene-H, $C_{2-10}$ alkynylene-H, $(CRR')_rO(CRR')_r$—H, $(CRR')_rNR^a(CRR')_r$—H, $(CRR')_rC(O)(CRR')_r$—H, $(CRR')_rC(O)O(CRR')_r$—H, $(CRR')_rOC(O)(CRR')_r$—H, $(CRR')_rC(O)NR^a(CRR')_r$—H, $(CRR')_rNR^aC(O)(CRR')_r$—H, $(CRR')_rOC(O)O(CRR')_r$—H, $(CRR')_rOC(O)NR^a(CRR')_r$—H, $(CRR')_rNR^aC(O)O(CRR')_r$—H, $(CRR')_rNR^aC(O)NR^a(CRR')_r$—H, $(CRR')_rS(O)_p(CRR')_r$—H, $(CRR')_rSO_2NR^a(CRR')_r$—H, $(CRR')_rNR^aSO_2(CRR')_r$—H, and $(CRR')_rNR^aSO_2NR^a(CRR')_r$—H;

alternatively, $R^3$ and $R^4$ combine to form a $C_{3-13}$ carbocyclic residue substituted with $R^c$ and 0–3 $R^b$ or a 5–14 membered heterocyclic system containing from 1–4 heteroatoms selected from the group consisting of N, O, and S and substituted with $R^c$ and 0–3 $R^b$;

$R^a$, at each occurrence, is independently selected from H, $C_{1-4}$ alkyl, phenyl and benzyl;

$R^{a'}$, at each occurrence, is independently selected from H, $C_{1-4}$ alkyl, phenyl and benzyl;

$R^{a''}$, at each occurrence, is independently selected from H, $C_{1-4}$ alkyl, benzyl, $C_{3-7}$ carbocyclic residue, or a 5 to 6 membered heteroaromatic ring containing 1–4 heteroatoms selected from the group consisting of N, O, and S;

alternatively, $R^a$ and $R^{a'}$ taken together with the nitrogen to which they are attached form a 4, 5, or 6 membered ring containing from 0–1 additional heteroatoms selected from the group consisting of N, O, and S;

$R^b$, at each occurrence, is independently selected from $C_{1-6}$ alkyl, $OR^a$, Cl, F, Br, I, =O, CN, $NO_2$, $NR^aR^{a'}$, $C(O)R^{a''}$, $C(O)OR^a$, $C(O)NR^aR^{a'}$, $S(O)_2NR^aR^{a'}$, $S(O)_pR^a$, $CF_3$, and $CF_2CF_3$;

$R^c$, at each occurrence, is independently selected from $C_{1-6}$ alkyl, $OR^a$, Cl, F, Br, I, =O, CN, $NO_2$, $NR^aR^{a'}$, $C(O)R^{a''}$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)$CH_3$, $(CRR')_sO(CRR')_sR^d$, $(CRR')_sS(O)_p$ $(CRR')_sR^d$, $(CRR')_sNR^a(CRR')_sR^d$, phenyl, and a 5–14 membered heterocyclic system containing from 1–4 heteroatoms selected from the group consisting of N, O, and S;

$R^5$, at each occurrence, is selected from H, $C_{1-10}$ alkyl substituted with 0–2 $R^b$, and $C_{1-8}$ alkyl substituted with 0–2 $R^d$;

$R^d$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system containing from 1–4 heteroatoms selected from the group consisting of N, O, and S and substituted with 0–3 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_{1-5}$ alkyl)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, —$CH(R^8)OC(=O)OR^9$, and

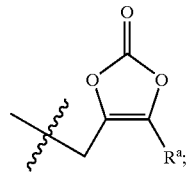

$R^7$ selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^e$, $C_{3-8}$ cycloalkyl substituted with 1–2 $R^e$, and phenyl substituted with 0–2 $R^b$;

$R^e$, at each occurrence, is selected from $C_{1-4}$ alkyl, $C_{3-8}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, 4, and 5;

r', at each occurrence, is selected from 0, 1, 2, 3, 4, and 5;

r", at each occurrence, is selected from 1, 2, and 3;

s, at each occurrence, is selected from 0, 1, 2, and 3; and, s', at each occurrence, is selected from 0, 1, 2, and 3.

In a preferred embodiment, the present invention provides a compound wherein;

A is selected from $COR^5$, —$CO_2H$, $CH(R)CO_2H$, —CONHOH, $CH(R)CONHOH$, —$CONHOR^5$, —$CONHOR^6$, —N(OH)$COR^5$, —SH, and —$CH_2SH$;

ring B is a 4–7 membered cyclic amide containing from 0–2 additional heteroatoms selected from O, $NR^a$, and $S(O)_p$, and 0–1 additional carbonyl groups and 0–1 double bonds;

U is absent;

X is absent;

Y is absent;

Z is selected from a C$_{5-10}$ carbocyclic residue substituted with 0–5 R$^b$ and a 5–10 membered heterocyclic system containing from 1–4 heteroatoms selected from the group consisting of N, O, and S and substituted with 0–5 R$^b$;

U$^a$ is absent or is selected from: O, NR$^a$, C(O), C(O)NR$^a$, NR$^a$C(O), OC(O)NR$^a$, NR$^a$C(O)O, NR$^a$C(O)NR$^a$, S(O)$_p$NR$^a$, and NR$^a$S(O)$_p$;

R$^2$ is selected from H, Q', C$_{1-5}$ alkylene-Q', C$_{2-5}$ alkenylene-Q', C$_{2-5}$ alkynylene-Q', (CRR')$_r$O(CRR')$_r$—Q', (CRR')$_r$NR$^a$(CRR')$_r$—Q', (CRR')$_r$NR$^a$C(O)(CRR')$_r$—Q', (CRR')$_r$C(O)NR$^a$(CRR')$_r$—Q', (CRR')$_r$NR$^a$C(O)NR$^a$(CRR')$_r$Q', (CRR')$_r$C(O)(CRR')$_r$—Q', (CRR')$_r$C(O)O(CRR')$_r$—Q', (CRR')$_r$S(O)$_p$(CRR')$_r$—Q, and (CRR')$_r$SO$_2$NR$^a$(CRR')$_r$—Q';

Q' is selected from H, phenyl substituted with 0–3 R$^b$ and a 5–6 membered heteroaryl system containing from 1–4 heteroatoms selected from the group consisting of N, O, and S and substituted with 0–3 R$^b$;

R$^3$ is selected from H, Q, C$_{1-10}$ alkylene-Q, C$_{2-10}$ alkenylene-Q, C$_{2-10}$ alkynylene-Q, (CRR')$_r$O(CRR')$_r$—Q, (CRR')$_r$NR$^a$(CRR')$_r$—Q, (CRR')$_r$C(O)(CRR')$_r$—Q, (CRR')$_r$NR$^a$C(O)(CRR')$_r$Q, (CRR')$_r$C(O)NR$^a$(CRR')$_r$—Q, (CRR')$_r$NR$^a$C(O)O(CRR')$_r$—Q, (CRR')$_r$NR$^a$C(O)NR$^a$(CRR')$_r$—Q, (CRR')$_r$S(O)$_p$(CRR')$_r$—Q, (CRR')$_r$SO$_2$NR$^a$(CRR')$_r$—Q, (CRR')$_r$NR$^a$SO$_2$(CRR')$_r$—Q, and (CRR')$_r$NR$^a$SO$_2$NR$^a$(CRR')$_r$—Q;

R, at each occurrence, is independently selected from H, CH$_3$, and CH$_2$CH$_3$;

R', at each occurrence, is independently selected from H and CH$_3$;

Q is selected from H, a C$_{3-10}$ carbocyclic residue substituted with 0–5 R$^b$ and a 5–10 membered heterocyclic system containing from 1–4 heteroatoms selected from the group consisting of N, O, and S and substituted with 0–5 R$^b$; and, R$^c$, at each occurrence, is independently selected from C$_{1-6}$ alkyl, OR$^a$, Cl, F, Br, I, =O, CN, NO$_2$, NR$^a$R$^{a'}$, C(O)R$^{a'}$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–10 membered heterocyclic system containing from 1–4 heteroatoms selected from the group consisting of N, O, and S.

In a more preferred embodiment, the present invention provides a compound wherein;

A is selected from —CO$_2$H, CH$_2$CO$_2$H, —CONHOH, CH(R)CONHOH, —CONHOR$^5$, and —N(OH)COR$^5$;

ring B is a 4–6 membered cyclic amide containing from 0–2 additional heteroatoms selected from O, NR$^a$, and S(O)$_p$, and 0–1 additional carbonyl groups and 0–1 double bonds;

Z is absent or selected from a C$_{5-6}$ carbocyclic residue substituted with 0–3 R$^b$ and a 5–9 membered heterocyclic system containing from 1–4 heteroatoms selected from the group consisting of N, O, and S and substituted with 0–5 R$^b$;

U$^a$ is absent or is selected from: O, NR$^a$, C(O), C(O)NR$^a$, NR$^a$C(O), and S(O)$_p$NR$^a$;

X$^a$ is absent or C$_{1-10}$ alkylene;

R$^2$ is selected from H, C$_{1-5}$ alkylene-Q', (CH$_2$)$_r$(CH$_2$)$_r$—Q', (CH$_2$)$_r$NR$^a$(CH$_2$)$_r$Q', (CRR')$_r$NR$^a$C(O)(CRR')$_r$Q', (CH$_2$)$_r$C(O)NR$^a$(CH$_2$)$_r$—Q', (CRR')$_r$NR$^a$C(O)NR$^a$(CRR')$_r$—Q', and (CH$_2$)$_r$C(O)(CH$_2$)$_r$—Q';

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–9 membered heterocyclic system containing from 1–4 heteroatoms selected from the group consisting of N, O, and S; and, Q is selected from H, a C$_{5-6}$ carbocyclic residue substituted with 0–5 R$^b$ and a 5–6 membered heterocyclic system containing from 1–4 heteroatoms selected from the group consisting of N, O, and S and substituted with 0–5 R$^b$.

In an even more preferred embodiment, the present invention provides a compound wherein;

A is selected from —CO$_2$H, CH$_2$CO$_2$H, —CONHOH, and —N(OH)CHO;

ring B is a 4–5 membered cyclic amide containing from 0–2 additional heteroatoms selected from O, NR$^a$, and S(O)$_p$, and 0–1 additional carbonyl groups and 0–1 double bonds;

X is absent or selected from C$_{1-4}$ alkylene, C$_{2-4}$ alkenylene, and C$_{2-4}$ alkynylene;

Z is absent or selected from phenyl substituted with 0–3 R$^b$ and a 5–9 membered aromatic heterocyclic system containing from 1–4 heteroatoms selected from the group consisting of N, O, and S and substituted with 0–3 R$^b$;

X$^a$ is absent or C$_{1-4}$ alkylene;

Y$^a$ is absent or selected from O and NR$^a$;

Z$^a$ is selected from H, a C$_{5-10}$ carbocyclic residue substituted with 0–5 R$^c$ and a 5–10 membered heterocyclic system containing from 1–4 heteroatoms selected from the group consisting of N, O, and S and substituted with 0–5 R$^c$;

R$^4$ is selected from H, C$_{1-4}$ alkylene-H, (CH$_2$)$_r$O(CH$_2$)$_r$—H, and (CH$_2$)$_r$NR$^a$(CH$_2$)$_r$—H; and, R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–6 membered heterocyclic system containing from 1–4 heteroatoms selected from the group consisting of N, O, and S.

In a preferred embodiment, the present invention provides a compound wherein;

(αS,3R)-α-[(2,2-dimethyl-1-oxopropyl)amino]-N-hydroxy-1-[4-[(2-methyl-4-quinolinyl)methoxy]phenyl]-2-oxo-3-pyrrolidineacetamide;

1,1-dimethylethyl [2-(hydroxyamino)-(1S)-1-[1-[4-[(2-methyl-4-quinolinyl)methoxy]phenyl]-2-oxo-(3R)-3-pyrrolidinyl]-2-oxoethyl]carbamate;

(αS,3R)-α-amino-N-hydroxy-1-[4-[(2-methyl-4-quinolinyl)methoxy]phenyl]-2-oxo-3-pyrrolidineacetamide;

(αS,3R)-α-(acetylamino)-N-hydroxy-1-[4-[(2-methyl-4-quinolinyl)methoxy]phenyl]-2-oxo-3-pyrrolidineacetamide;

N-[2-(hydroxyamino)-(1S)-1-[1-[4-[(2-methyl-4-quinolinyl)methoxy]phenyl]-2-oxo-(3R)-3-pyrrolidinyl]-2-oxoethyl]-4-morpholinecarboxamide;

1,1-dimethylethyl [(1S)-1-[1-[4-[(2,6-dimethyl-4-pyridinyl)methoxy]phenyl]-2-oxo-(3R)-3-pyrrolidinyl]-2-(hydroxyamino)-2-oxoethyl]carbamate;

(αS,3R)-α-amino-1-[4-[(2,6-dimethyl-4-pyridinyl)methoxy]phenyl]-N-hydroxy-2-oxo-3-pyrrolidineacetamide;

methyl (1S)-2-(hydroxyamino)-1-((3R)-1-{4-[(2-methyl-4-quinolinyl)methoxy]phenyl}-2-oxopyrrolidinyl)-2-oxoethylcarbamate;

butyl (1S)-2-(hydroxyamino)-1-((3R)-1-{4-[(2-methyl-4-quinolinyl)methoxy]phenyl}-2-oxopyrrolidinyl)-2-oxoethylcarbamate;

N-[(1S)-2-(hydroxyamino)-1-((3R)-1-{4-[(2-methyl-4-quinolinyl)methoxy]phenyl}-2-oxopyrrolidinyl)-2-oxoethyl]benzamide;

(2S)-N-hydroxy-2-((3R)-1-{4-[(2-methyl-4-quinolinyl)methoxy]phenyl}-2-oxopyrrolidinyl)-2-(1H-pyrrol-1-yl)ethanamide;

(2S)-2-(dimethylamino)-N-hydroxy-2-((3R)-1-{4-[(2-methyl-4-quinolinyl)methoxy]phenyl}-2-oxopyrrolidinyl)ethanamide;

(2R)-N-hydroxy-2-((3R)-1-{4-[(2-methyl-4-quinolinyl)methoxy]phenyl}-2-oxopyrrolidinyl)propanamide;

(2S)-N-hydroxy-2-((3R)-1-{4-[(2-methyl-4-quinolinyl)methoxy]phenyl}-2-oxopyrrolidinyl)propanamide;

(2R)-N-hydroxy-2-((3R)-1-{4-[(2-methyl-4-quinolinyl)methoxy]phenyl}-2-oxopyrrolidinyl)pentanamide;

(2S)-N,2-dihydroxy-2-((3R)-1-{4-[(2-methyl-4-quinolinyl)methoxy]phenyl}-2-oxopyrrolidinyl)ethanamide;

(1S)-1-{(3R)-1-[4-(benzyloxy)phenyl]-2-oxopyrrolidinyl}ethyl(hydroxy)formamide;

hydroxy[(1S)-1-((3R)-1-{4-[(2-methyl-4-quinolinyl)methoxy]phenyl}-2-oxopyrrolidinyl)ethyl]formamide;

(2R,S)-((3S,R)-3-amino-1-{4-[2-methyl-4-quinolinyl)methoxy]phenyl}-2-oxopyrrolidinyl)-N-hydroxypentanamide;

(2S,R)-((3S,R)-3-amino-1-{4-[2-methyl-4-quinolinyl)methoxy]phenyl}-2-oxopyrrolidinyl)-N-hydroxypentanamide;

(2S,R)-((3S,R)-3-amino-1-{4-[2-methyl-4-quinolinyl)methoxy]phenyl}-2-oxopyrrolidinyl)-N-hydroxypropanamide;

(2S,R)-((3S,R)-3-(dimethylamino)-1-{f4-[2-methyl-4-quinolinyl)methoxy]phenyl}-2-oxopyrrolidinyl)-N-hydroxypropanamide; and, 2-((3S,R)-3-amino-1-{4-[2-methyl-4-quinolinyl)methoxy]phenyl}-2-oxopyrrolidinyl)-N-hydroxyacetamide;

or a pharmaceutically acceptable salt form thereof.

In another embodiment, the present invention provides a novel pharmaceutical composition, comprising: a pharmaceutically acceptable carrier and a therapeutically effective amount of a compound of formula I or a pharmaceutically acceptable salt form thereof.

In another embodiment, the present invention provides a novel method for treating or preventing an inflammatory disorder, comprising: administering to a patient in need thereof a therapeutically effective amount of a compound of formula I or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula I or a pharmaceutically acceptable salt form thereof.

In another embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula I or a pharmaceutically acceptable salt form thereof.

In another embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula I or a pharmaceutically acceptable salt form thereof.

In another embodiment, the present invention provides novel lactams of formula I for use in therapy.

In another embodiment, the present invention provides the use of novel lactams of formula I for the manufacture of a medicament for the treatment of an inflammatory disorder.

In another embodiment, the present invention provides the use of novel lactams of formula I for the manufacture of a medicament for the treatment of a condition or disease mediated by MMPs, TNF, aggrecanase, or a combination thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^b$, then said group may optionally be substituted with up to two $R^b$ groups and $R^b$ at each occurrence is selected independently from the definition of $R^b$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon-carbon bonds which may occur in any stable point along the chain, such as ethenyl and propenyl. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl and propynyl. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-thiazolyl, 1,2, 4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit a MMP related disorder in a host. The combination of compounds is preferably a synergistic combination. Synergy, as described for example by Chou and Talalay, Adv. Enzyme Regul. 22:27–55 (1984), occurs when the effect (in this case, inhibition of a MMP) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased inhibitory effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated herein in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A variety of compounds of formula (I) wherein ring B is pyrrolidinone or piperidinone can be prepared by methods described in Scheme 1. Carboxylic acid 1 can be converted to 3 under several sets of literature conditions. One example is activation of 1 with trimethylacetyl chloride followed by treatment with 2. Alkylation of 3 with methyl bromoacetate or t-butyl bromoacetate provides 4a or 4b, respectively. 4a and 4b are converted to aldehydes 5a and 5b by oxidative degradation, such as ozonolysis, or dihydroxylation ($OSO_4$) followed by cleavage with $NaIO_4$. The desired pyrrolidinone 7a and piperidinone 7b are synthesized upon treatment of aldehyde 5 and appropriately functionalized amine 6 with zinc in acetic acid at elevated temperature. Alternatively, 5 and 6 are first coupled to form imine in toluene at reflux, then reduced with reducing agent such as sodium triacetoxyborohydride, and finally cyclized at elevated temperature. As another alternative route to 7b, 4b is hydrolyzed to give carboxylic acid 8. 8 is coupled to an appropriately substituted amine 6 by methods well described in the literature for making amide bonds, such as BOP-Cl in THF, to give compound 9. Following oxidative cleavage as described previously, the resultant aldehyde 10 is treated with reducing agents such as triethylsilane in the presence of acids such as trifluoroacetic acid to provide 7b.

Scheme 1

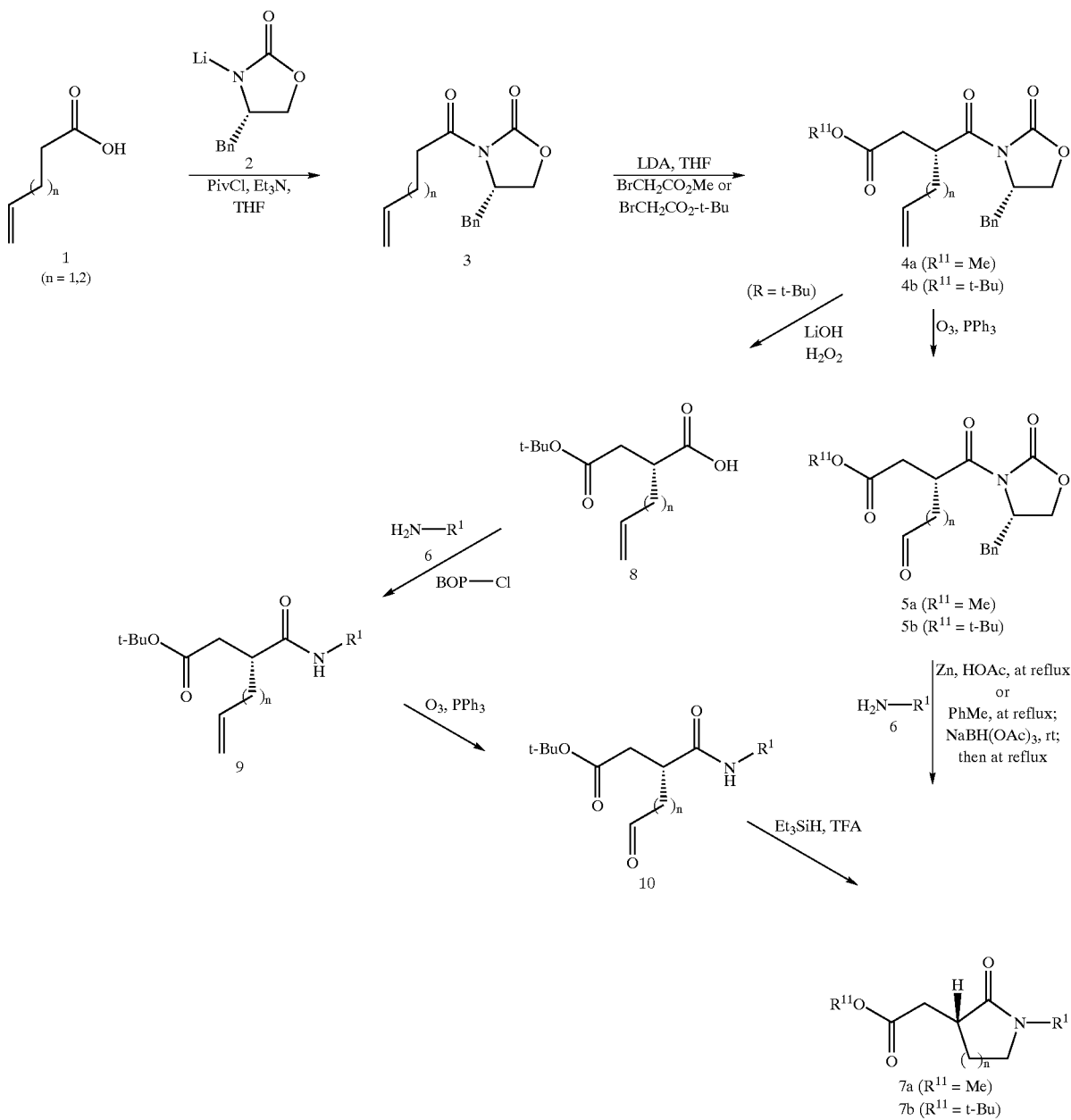

The methyl ester of 7 ($R^{11}$=Me) is converted to hydroxamic acid 11 by treatment with hydroxylamine under basic conditions such as KOH or NaOMe in solvents such as methanol (Scheme 2). The methyl ester 7 ($R^{11}$=Me) can also be converted to O-benzyl protected hydroxamic acid with O-benzylhydroxylamine under similar conditions or using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). The benzyl ether is removed by methods well known in the literature such as hydrogenation using palladium on barium sulfate in hydrogen, to give compound 11. Alternatively, 11 can be prepared through the carboxylic intermediate 12. Carboxylic acid 12 is converted to 11 via coupling with hydroxylamine or O-benzylhydroxylamine followed by deprotection.

Scheme 2

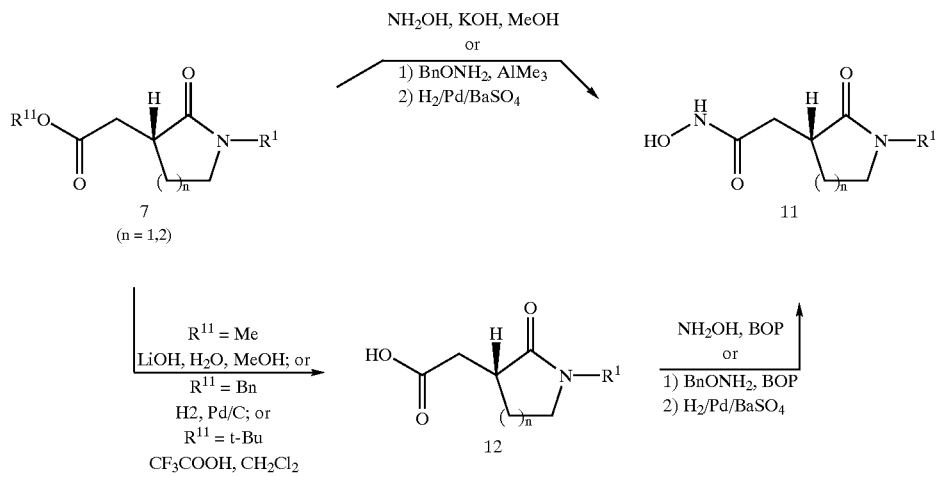

A variety of compounds of formula (I) wherein ring B is pyrrolidinone or piperidinone and $R^3$ is alkyl can be prepared by methods described in Scheme 3. Following known literature procedure (Becket, R. P.; Crimmins, M. J.; Davis, M. H.; Spavold, Z. *Synlett* 1993, 137), intermediate 8 from Scheme 1 is converted to anti-succinate 14 via alkylation and epimerization. Following esterification and olefin cleavage, the aldehyde 16 is converted to lactam 17 following conditions as described previously. Ester 17 is converted to the hydroxamic acid following the sequences outlined in Scheme 2.

Scheme 3

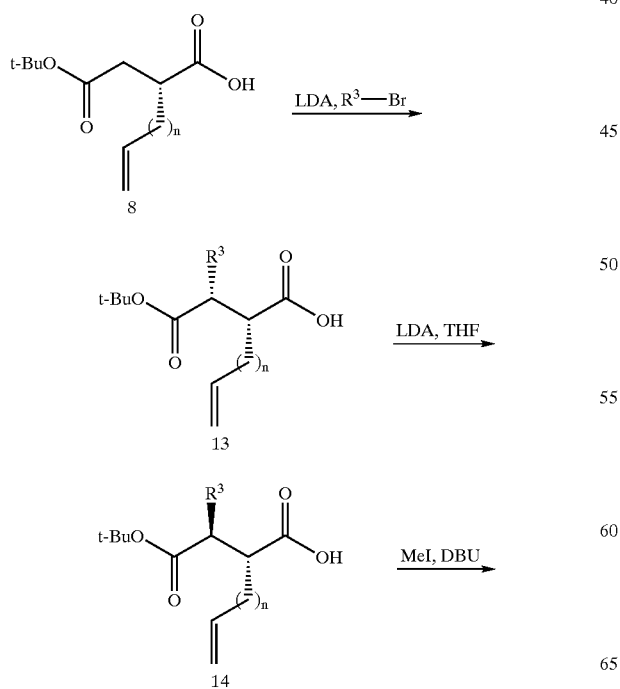

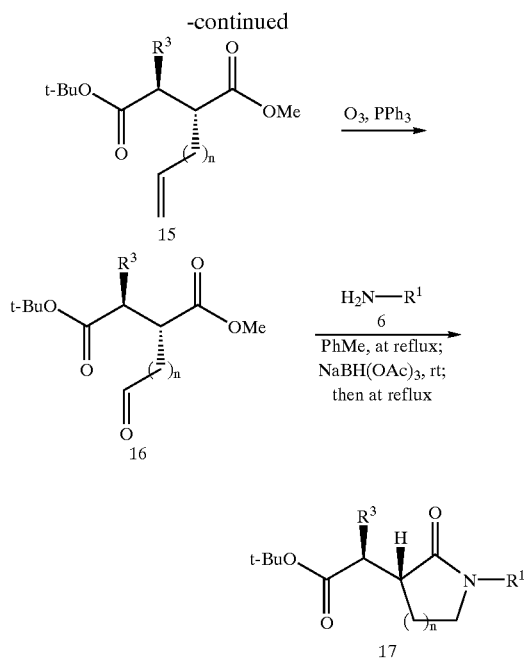

A variety of compounds of formula (I) wherein ring B is imidazolinone or piperazinone can be prepared by methods described in Scheme 4. Esterification of D-aspartic acid 18 and alkylation provide anti-alkylated product 20. Cleavage of benzyl ester, coupling with appropriately functionalized amine 6 under conditions described previously and unmasking of the amino group gives 23. The imidazolinone ring formation is achieved with formaldehyde in solvent such as toluene at elevated temperature. The piperazinone analogues can be synthesized from common intermediate 21. Following coupling with appropriately functionalized amine 25 and olefin cleavage, the aldehyde 27 is converted to piperazinone 28 following conditions as described previously. The secondary amine center of 28 is further functionalized as tertiary amines, amides, sulfonamides, carbamates, ureas, or sulfonylureas (29). Esters 24, 28 and 29 are converted to the hydroxamic acids following the sequences outlined in Scheme 2.

Scheme 4

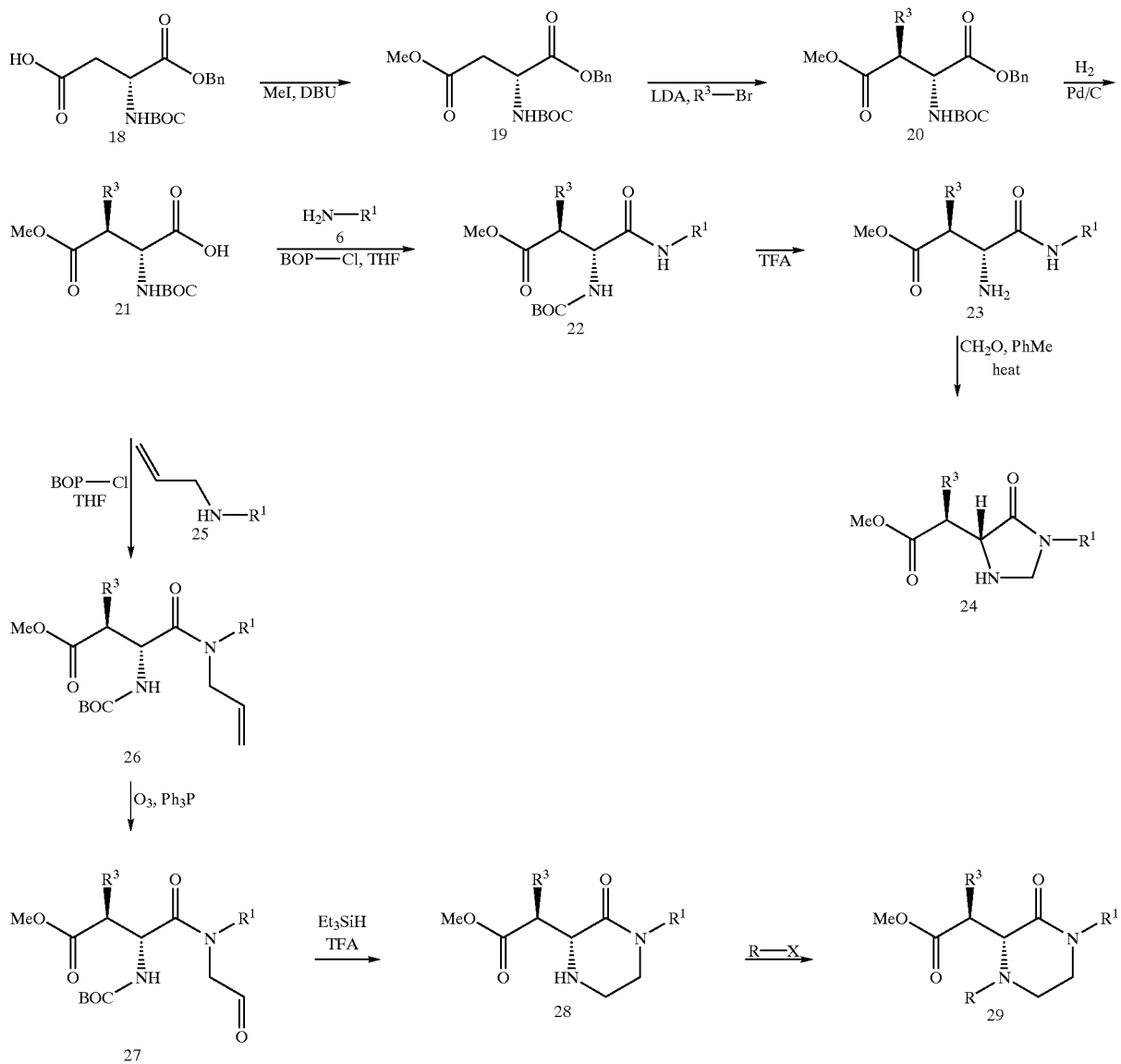

A variety of compounds of formula (I) wherein $R^3$ is an amino derivative can be prepared by methods described in Scheme 5. L-Aspartic acid 30 is converted to 32 following similar sequence described earlier. Oxidative cleavage of 32 yields aldehyde 33 (n=1), an intermediate for pyrrolidinones. The corresponding intermediate for piperidinones, 33 (n=2), is synthesized by hydroboration with agents such as 9-BBN and oxidation following methods well described in the literature, such as Swern oxidation. 33 is converted to 34 following conditions described previously. After removal of BOC group, The primary amine center of 35 is further functionalized as secondary or tertiary amines, amides, sulfonamides, carbamates, ureas, or sulfonylureas (36 and 37). Esters 34–37 are converted to the hydroxamic acids following the sequences outlined in Scheme 2.

Scheme 5

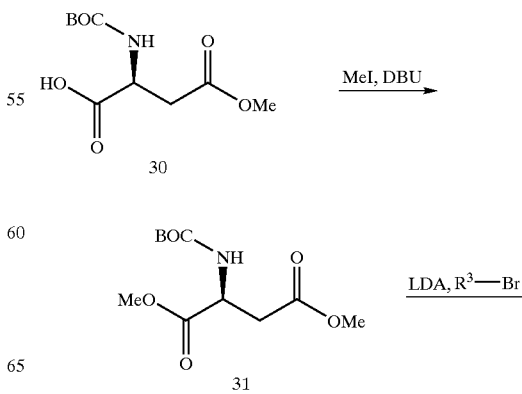

-continued

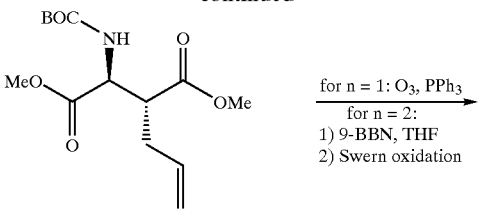
32

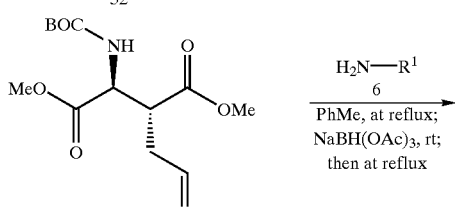
33 (n = 1,2)

for n = 1: O₃, PPh₃
for n = 2:
1) 9-BBN, THF
2) Swern oxidation

H₂N—R¹
6
PhMe, at reflux;
NaBH(OAc)₃, rt;
then at reflux

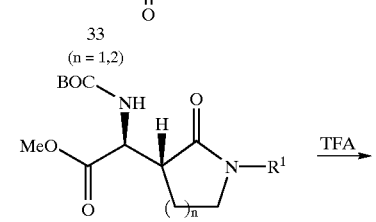
34

TFA

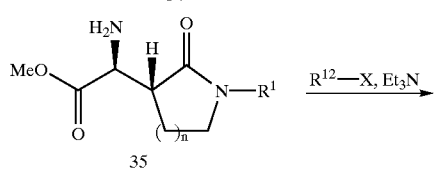
35

R¹²—X, Et₃N

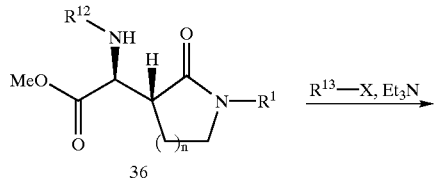
36

R¹³—X, Et₃N

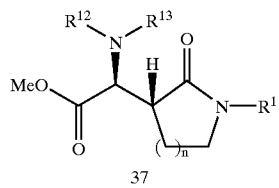
37

A variety of compounds of formula (I) wherein R³ is OR can be prepared by methods described in Scheme 6. Frater alkylation of dimethyl malate (38) establishes the anti configuration. 39 is converted to 41 using chemistry described previously. The hydroxyl group in 41 is functionalized as ethers, esters, carbonates or urethanes (42). Esters 41–42 are converted to the hydroxamic acids following the sequences outlined in Scheme 2.

Scheme 6

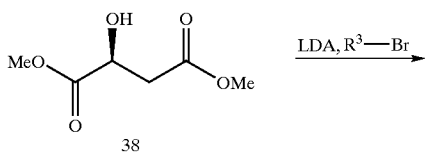
38

LDA, R³—Br

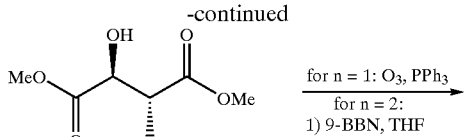
39 for n = 1: O₃, PPh₃
for n = 2:
1) 9-BBN, THF
2) Swern oxidation

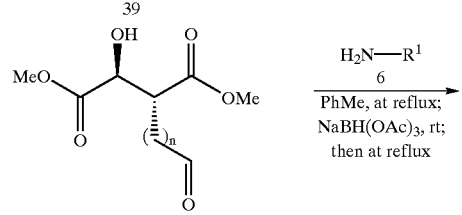
40 (n = 1,2)

H₂N—R¹
6
PhMe, at reflux;
NaBH(OAc)₃, rt;
then at reflux

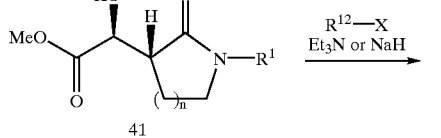
41

R¹²—X
Et₃N or NaH

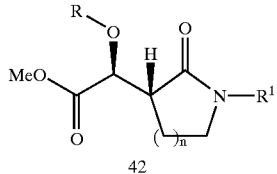
42

A variety of compounds of formula (I) wherein A is —NH(OH)C(O)H can be prepared by methods described in Scheme 7. Frater alkylation, and Wenreib amide formation with O-t-butylhydroxylamine give 45. β-Lactam formation is done by mesylate formation and base-induced lactamization. TMSCl mediated methanolysis followed by N-formylation provide 49. Following sequence analogous to that described in previous schemes, lactam 51 is obtained. Hydrolysis of t-Butyl group in 51 completes the synthesis.

Scheme 7

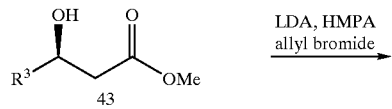
43

LDA, HMPA
allyl bromide

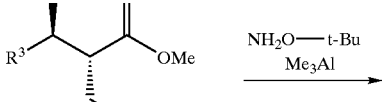
44

NH₂O—t-Bu
Me₃Al

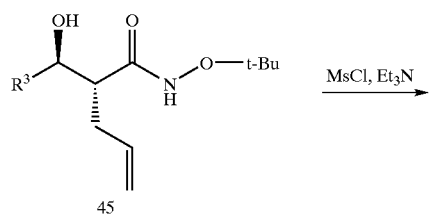
45

MsCl, Et₃N

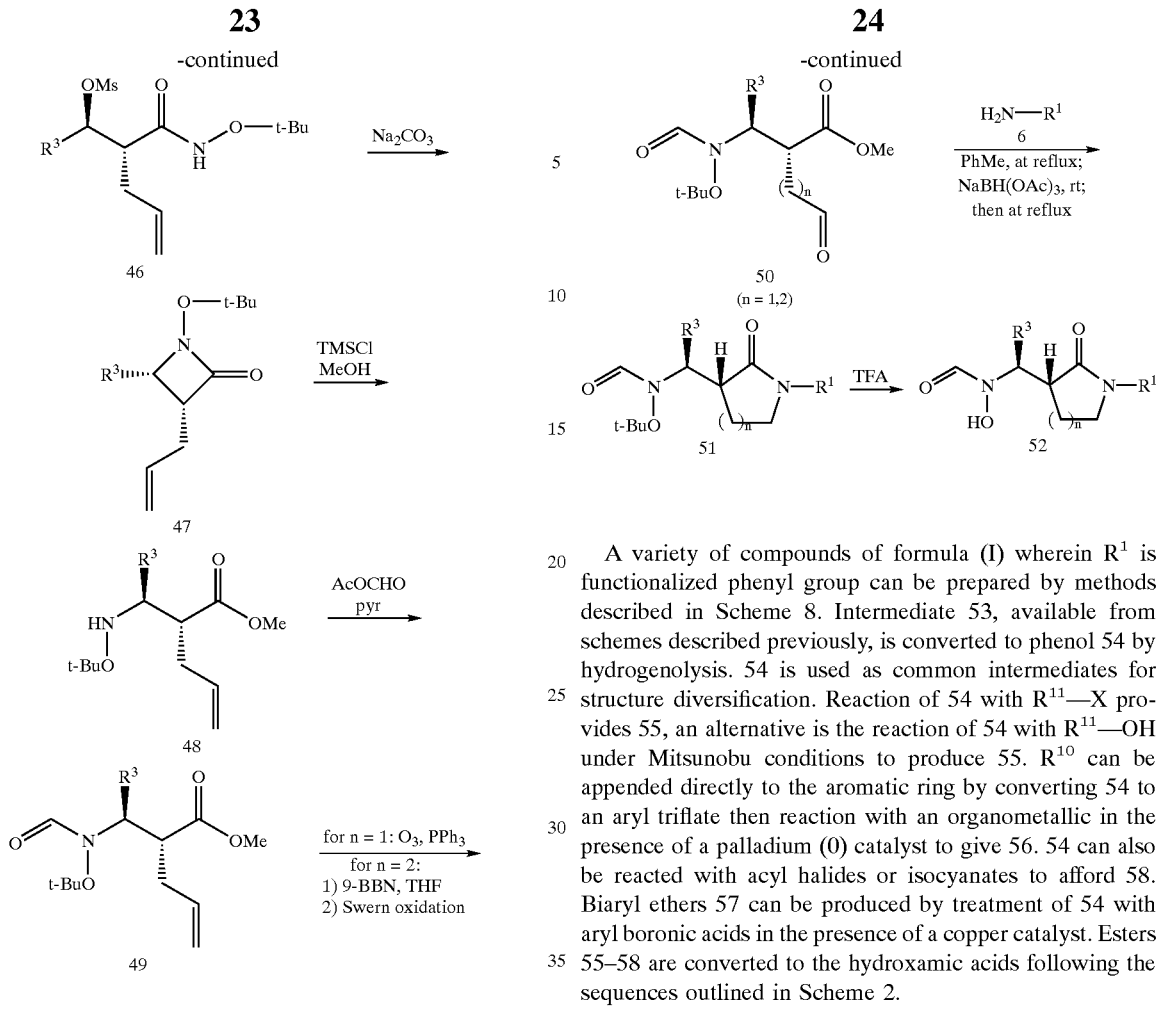

A variety of compounds of formula (I) wherein $R^1$ is functionalized phenyl group can be prepared by methods described in Scheme 8. Intermediate 53, available from schemes described previously, is converted to phenol 54 by hydrogenolysis. 54 is used as common intermediates for structure diversification. Reaction of 54 with $R^{11}$—X provides 55, an alternative is the reaction of 54 with $R^{11}$—OH under Mitsunobu conditions to produce 55. $R^{10}$ can be appended directly to the aromatic ring by converting 54 to an aryl triflate then reaction with an organometallic in the presence of a palladium (0) catalyst to give 56. 54 can also be reacted with acyl halides or isocyanates to afford 58. Biaryl ethers 57 can be produced by treatment of 54 with aryl boronic acids in the presence of a copper catalyst. Esters 55–58 are converted to the hydroxamic acids following the sequences outlined in Scheme 2.

Scheme 8

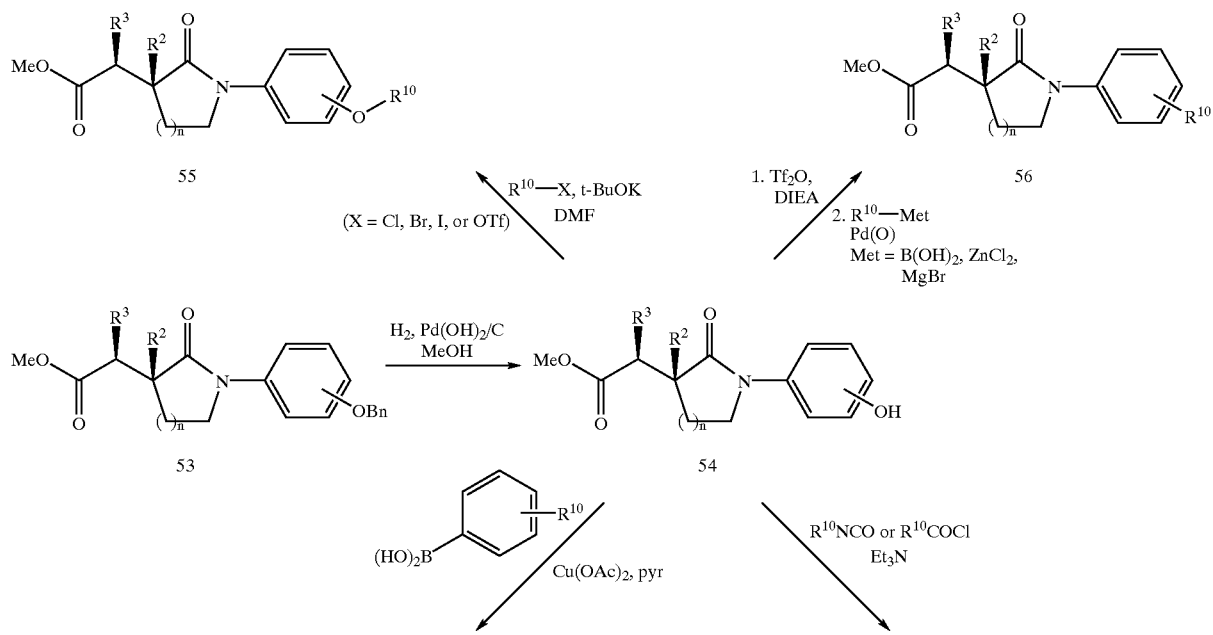

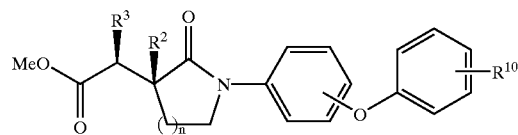

57

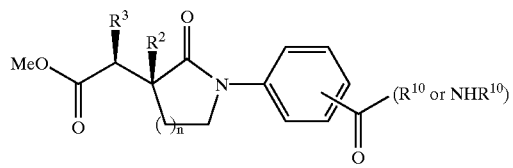

58

A variety of compounds of formula (I) wherein $R^2$ is an amino derivative can be prepared by methods described in Scheme 9. Protecting group manipulations on 59 give 61. Allylation and esterification gives 63. 63 is converted to lactam 65 following previously described sequences. Allylation and hydrogenation provide phenol 67. 67 can be functionalized following scheme 8 and converted to hydroxamic acid following scheme 2.

Scheme 9

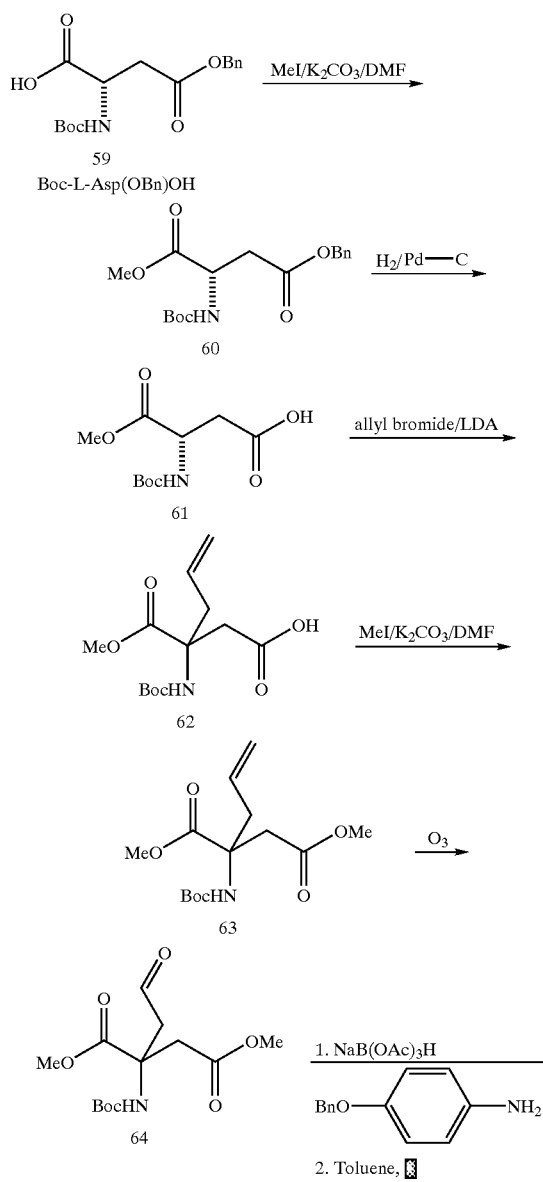

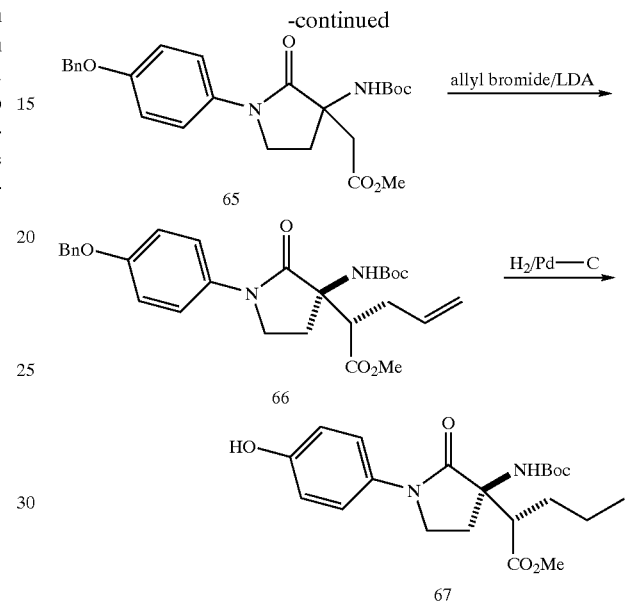

Aternatively, phenol 67 can be prepared following scheme 10. Allylation of 60 gives 68 with the desired anti configuration. Following hydrogenation, 69 is further allylated and protected as methyl ester. 70 is then converted to phenol 67 following previously described sequences.

Scheme 10

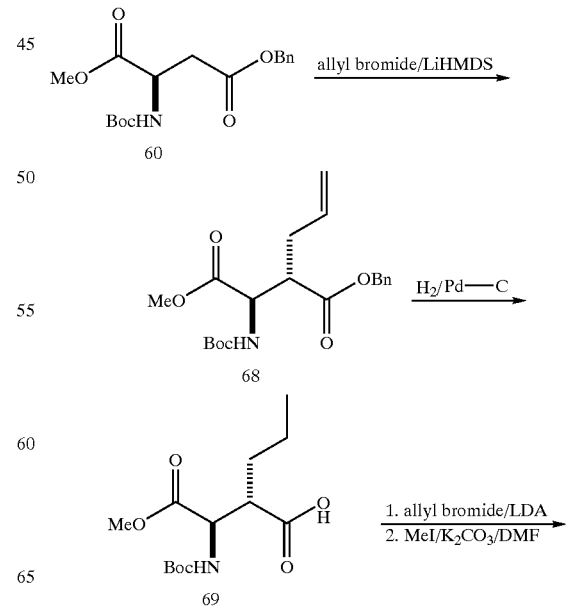

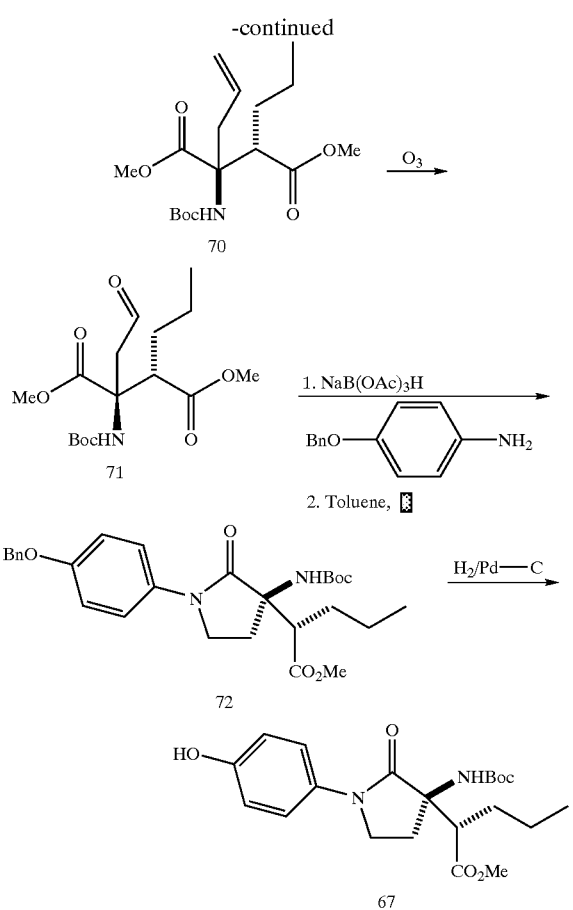

One diastereomer of a compound of Formula I may display superior activity compared with the others. Thus, the following stereochemistries are considered to be a part of the present invention.

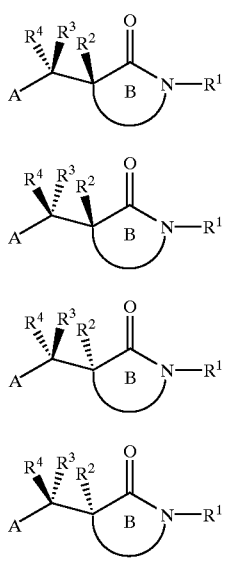

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tert. lett*. 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

(αS,3R)-α-[(2,2-Dimethyl-1-oxopropyl)amino]-N-Hydroxy-1-[4-[(2-methyl-4-quinolinyl)methoxy] phenyl]-2-oxo-3-pyrrolidineacetamide mono (Trifluoroacetate)

(1a) Iodomethane (31.5 mL, 2.5 eq) was added to a mixture of N-t-BOC-L-Asp β-methyl ester (50.0 g, 202 mmol) and DBU (36.3 mL, 1.2 eq) in toluene (800 mL) at 0° C. and the mixture was allowed to stir at rt overnight. The resulting suspension was filtered. The filtrate was concentrated and filtered through a pad of silica gel. The filter cake was washed with ether until free of product. The filtrate was concentrated to give the desired ester (47.0 g, 89%) as a solid. MS found: (M+H)$^+$=262.

(1b) A 1 M THF solution of LiHMDS (392 mL, 2.2 eq) was added to a solution of the ester from (1a) (46.5 g, 178 mmol) in toluene (1800 mL) and THF (210 mL) at −78° C. After 1 h at this temperature, allyl bromide (30.8 mL, 2 eq) was added dropwise. The mixture was stirred at −40 to −50° C. for 20 h and quenched by addition of saturated NH$_4$Cl. After removal of THF in vacuo, the aqueous residue was extracted with ethyl acetate (3×300 mL). The combined organic extracts were dried (MgSO$_4$), and concentrated. Silica gel chromatography (ethyl acetate-hexane, 10:90 then 20:80) provided the desired product (25.9 g, 48%). MS found: (M+H)$^+$=302.

(1c) Ozone was bubbled through a solution of the olefin from (1b) (25.8 g, 85.6 mmol) in dichloromethane (600 mL) at −78° C. until starting material disappeared as judged by TLC. The mixture was purged with nitrogen and treated with triphenylphosphine (26.9 g, 1.2 eq). After 4 h at ambient temperature, the mixture was concentrated in vacuo and purified by silica gel chromatography (ethyl acetate-hexane, 30:70 then 40:60) to give the desired product (18.4 g, 71%) as an inter-converting mixture of aldehyde and cyclic aminal. MS found: (M+Na)$^+$=326.

(1d) A solution of the intermediate from (1c) (8.00 g, 26.3 mmol) and 4-benzyloxyaniline (5.25 g, 1 eq) in toluene (300 mL) was heated to reflux for 6 h with azotropic removal of water with a Dean-Stark trap. The resultant imine solution was cooled to room temperature, and treated with sodium triacetoxyborohydride (7.25, 1.3 eq). After 48 h at rt, the imine reduction was still incomplete.

Toluene was removed in vacuo. The residue was dissolved in 1,2-dichloroethane (60 mL) and treated with additional sodium triacetoxyborohydride (1 eq). After 6 h at rt, the imine reduction was complete as judged by MS analysis. Following addition of ethyl acetate (600 mL) and saturated sodium bicarbonate (30 mL), the mixture was washed with water (2×30 mL), brine (30 mL), dried (MgSO$_4$) and concentrated. The crude material was dissolved in toluene (200 mL) and heated to reflux overnight. Removal of solvent in vacuo and silica gel chromatography (ethyl acetate-hexane, 30:70) gave the desired lactam (5.91 g, 46%). MS found: (M+H)$^+$=455.

(1e) The lactam from (1d) (5.90 g, 12.2 mmol) and 20% palladium hydroxide on carbon (1.50 g) in methanol (200 mL) was stirred under balloon pressure hydrogen for 3 h. Following removal of catalyst by filtration, the filtrate was concentrated and purified by silica gel chromatography (ethyl acetate-hexane, 40:60 then 50:50) to give the desired phenol (3.30 g, 74%). MS found: (M+H)$^+$=365.

(1f) Cesium carbonate (5.10 g, 3.8 eq) was added to a mixture of the phenol from (1e) (1.50 g, 4.12 mmol), 4-chloromethyl-2-methylquinoline hydrochloride (1.88 g, 2 eq), sodium iodide (1.32 g, 2 eq) and methyl sulfoxide (20 mL). After 2 h at room temperature, the reaction was quenched with saturated ammonium chloride (20 mL) and diluted with ethyl acetate (400 mL). The mixture was washed with water (2×20 mL), brine (20 mL), dried (MgSO$_4$) and concentrated. Silica gel chromatography (ethyl acetate-hexane, 70:30) gave the desired product (1.83 g, 86%). MS found: (M+H)$^+$=520.

(1g) The intermediate from (1f) (1.73 g, 3.33 mmol) was stirred in trifluoroacetic acid (10 mL) and dichloromethane (10 mL) at room temperature for 2 h and concentrated to give the free amine (2.91 g, 100%) as a trifluoroacetate salt. MS found: (M+H)$^+$=420.

(1h) Diisopropylethylamine (0.27 mL, 6 eq) and trimethylacetyl chloride (1.1 eq) were added to the amine from (1g) (250 mg, 0.258 mmol) in dichloromethane (6 mL) at 0° C. After 10 min at this temperature, saturated sodium bicarbonate (3 mL) and ethyl acetate (60 mL) were added. The mixture was washed with water (2×5 mL), brine (5 mL), dried (MgSO$_4$) and concentrated. The crude material was taken to the next step without purification. MS found: (M+H)$^+$=586.

(1i) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The freshly prepared 1.76 M solution of hydroxylamine (3.2 mL, 25 eq) pre-cooled to 0° C. was added to the crude methyl ester from (1h) at 0° C. After 1 h at this temperature, the mixture was acidified to pH 4–5 by addition of 1 N HCl and purified by reverse phase HPLC on a Dynamax-60A C-18 column eluting an acetonitrile:water:TFA gradient, to give the desired hydroxamic acid (0.085 g, 55% for 2 steps). MS (M+H)$^+$=487.

Example 2

1,1-Dimethylethyl [2-(Hydroxyamino)-(1S)-1-[1-[4-[(2-methyl-4-quinolinyl)methoxy]phenyl]-2-oxo-(3R)-3-pyrrolidinyl]-2-oxoethyl]carbamate mono (Trifluoroacetate)

Following the procedures analogous to that used for step (1i), but using the lactam from step (1f) the title compound was prepared. The product was purified by reverse phase HPLC on a Dynamax-60A C-18 column eluting an acetonitrile:water:TFA gradient, to give the hydroxamic acid product. MS (M+H)$^+$=521.

Example 3

(αS,3R)-α-Amino-N-hydroxy-1-[4-[(2-methyl-4-quinolinyl)methoxy]phenyl]-2-oxo-3-pyrrolidineacetamide bis(Trifluoroacetate)

Following the procedures analogous to that used for step (1g), the material from example 2 was converted to the title compound. MS (M+H)$^+$=421.

Example 4

(αS,3R)-α-(Acetylamino)-N-Hydroxy-1-[4-[(2-methyl-4-quinolinyl)methoxy]phenyl]-2-oxo-3-pyrrolidineacetamide mono(Trifluoroacetate)

Beginning with the amine from (1g) and acetic anhydride, the title compound was prepared in an analogous series of reations to (1h) and (1i). The product was purified by reverse phase HPLC on a Dynamax-60A C-18 column eluting an acetonitrile:water:TFA gradient, to give the hydroxamic acid product. MS found: (M+H)$^+$=463.

Example 5

N-[2-(Hydroxyamino)-(1S)-1-[1-[4-[(2-methyl-4-quinolinyl)methoxy]phenyl]-2-oxo-(3R)-3-pyrrolidinyl]-2-oxoethyl]-4-morpholinecarboxamide mono(Trifluoroacetate)

Beginning with the amine from (1g) and 4-morpholinecarbonyl chloride, the title compound was prepared in an analogous series of reactions to (1h) and (1i). The product was purified by reverse phase HPLC on a Dynamax-60A C-18 column eluting an acetonitrile:water:TFA gradient, to give the hydroxamic acid product. MS found: (M+H)$^+$=534.

Example 6

1,1-Dimethylethyl [(1S)-1-[1-[4-[(2,6-Dimethyl-4-pyridinyl)methoxy]phenyl]-2-oxo-(3R)-3-pyrrolidinyl]-2-(hydroxyamino)-2-oxoethyl] carbamate mono(Trifluoroacetate)

Beginning with the phenol from (1e) and 4-chloromethyl-2,6-dimethylpyridine, the title compound was prepared in an analogous series of reactions to (1f) and (1i). The product was purified by reverse phase HPLC on a Dynamax-60A C-18 column eluting an acetonitrile:water:TFA gradient, to give the hydroxamic acid product. MS found: (M+H)$^+$=485.

Example 7

(αS,3R)-α-Amino-1-[4-[(2,6-dimethyl-4-pyridinyl)methoxy]phenyl]-N-hydroxy-2-oxo-3-pyrrolidineacetamide bis(Trifluoroacetate)

Following the procedures analogous to that used for step (1g), the material from example 6 was converted to the title compound. MS (M+H)$^+$=387.

Example 8

Methyl (1S)-2-(Hydroxyamino)-1-((3R)-1-{4-[(2-methyl-4-quinolinyl)methoxy]phenyl}-2-oxopyrrolidinyl)-2-oxoethylcarbamate mono (Trifluoroacetate)

Beginning with the amine from (1g) and methyl chloroformate, the title compound was prepared in an analogous series of reactions to (1h) and (1i). The product was purified by reverse phase HPLC on a Dynamax-60A C-18 column eluting an acetonitrile:water:TFA gradient, to give the hydroxamic acid product. MS found: $(M+H)^+=479$.

Example 9

Butyl (1S)-2-(Hydroxyamino)-1-((3R)-1-{4-[(2-methyl-4-quinolinyl)methoxy]phenyl}-2-oxopyrrolidinyl)-2-oxoethylcarbamate mono (Trifluoroacetate)

Beginning with the amine from (1g) and n-butyl chloroformate, the title compound was prepared in an analogous series of reactions to (1h) and (1i). The product was purified by reverse phase HPLC on a Dynamax-60A C-18 column eluting an acetonitrile:water:TFA gradient, to give the hydroxamic acid product. MS found: $(M+H)^+=520$.

Example 10

N-[(1S)-2-(Hydroxyamino)-1-((3R)-1-{4-[(2-methyl-4-quinolinyl)methoxy]phenyl}-2-oxopyrrolidinyl)-2-oxoethyl]benzamide mono (Trifluoroacetate)

Beginning with the amine from (1g) and benzoyl chloride, the title compound was prepared in an analogous series of reactions to (1h) and (1i). The product was purified by reverse phase HPLC on a Dynamax-60A C-18 column eluting an acetonitrile:water:TFA gradient, to give the hydroxamic acid product. MS found: $(M+H)^+=525$.

Example 11

(2S)-N-Hydroxy-2-((3R)-1-{4-[(2-Methyl-4-quinolinyl)methoxy]phenyl}-2-oxopyrrolidinyl)-2-(1H-pyrrol-1-yl)ethanamide mono(Trifluoroacetate)

(11a) Tetrahydro-2,5-dimethoxyfuran (22.7 mg, 1.2 eq) was added to the amine from (1g) (125 mg, 0.143 mmol) in water (0.5 mL) and 1,2-dichloroethane (0.5 mL). The mixture was vigorously stirred at 80° C. for 1h, and cooled to room temperature. Following addition of ethyl acetate (50 mL), the mixture was washed with water (2 mL) and brine (2 mL), dried ($MgSO_4$) and concentrated. Silica gel column chromatography (methanol-dichloromethane, 5:95) provided the desired pyrrole (45 mg, 68%). MS found: $(M+H)^+=470$.

(11b) Following the procedures analogous to that used for step (1i), but using the lactam from step (11a) the title compound was prepared. The product was purified by reverse phase HPLC on a Dynamax-60A C-18 column eluting an acetonitrile:water:TFA gradient, to give the hydroxamic acid product. MS $(M+H)^+=471$.

Example 12

(2S)-2-(Dimethylamino)-N-Hydroxy-2-((3R)-1-{4-[(2-methyl-4-quinolinyl)methoxy]phenyl}-2-oxopyrrolidinyl)ethanamide bis(Trifluoroacetate)

(12a) A mixture of the amine from (1g) (500 mg, 0.572 mmol), 37% aqueous formaldehyde (46 mg, 1 eq), and DIEA (0.6 ml, 6 eq) in 1,2-dichloroethane (10 mL) was stirred at rt for 2 h. Sodium triacetoxyborohydride (182 mg, 1.5 eq) was added and the mixture stirred overnight. Analysis of an aliquot indicated the mixture contains mostly dimethylated product and unreacted starting material, but very little mono-methylated product. Therefore, the mixture was converted to fully dimethylated product by treating with additional formaldehyde (1.1 eq) and sodium triacetoxyborohydride (1.3 eq) for 4 h. Following addition of sat. $NaHCO_3$ (5 mL) and ethyl acetate (100 mL), the mixture was washed with water (2×5 mL), brine (5 mL), dried ($MgSO_4$) and concentrated to give crude product (260 mg), which was taken to next step without purification. MS found: $(M+H)^+=448$.

(12b) Following the procedures analogous to that used for step (1i), but using the crude material from step (12a) (200 mg) the title compound was prepared. The product was purified by reverse phase HPLC on a Dynamax-60A C-18 column eluting an acetonitrile:water:TFA gradient, to give the hydroxamic acid product (112 mg, 37% for two steps). MS $(M+H)^+=449$.

Example 13

(2R)-N-Hydroxy-2-((3R)-1-{4-[(2-methyl-4-quinolinyl)methoxy]phenyl}-2-oxopyrrolidinyl) propanamide mono(Trifluoroacetate)

(13a) Pivaloyl chloride (16.04 mL, 1.05 eq) was added to a solution of 4-pentenoic acid (13.08 g, 1.05 eq) and triethylamine (20.74 mL, 1.2 eq) in THF (500 mL) at −78° C. The suspension was stirred at −78° C. for 10 min, 0° C. for 30 min and cooled to −78° C. In a separate flask, a 2.5 M hexane solution of n-BuLi (49.6 mL, 1 eq) was added to a solution of (S)-4-benzyloxazolidinone (21.97 g, 124 mmol) in THF (400 mL) at −78° C. The cold lithiated oxazolidinone solution was added via a canula to the mixed anhydride solution. The mixture was stirred at 0° C. for 30 min and quenched with saturated $NH_4Cl$ (300 mL). After removal of THF in vacuo, the aqueous residue was extracted with 1:2 mixture of ether-hexane (3×250 mL). The combined extracts were washed with water (20 mL), brine (20 mL), dried ($MgSO_4$), and concentrated. Silica gel column chromatography (ethyl acetate-hexane, 15:85 then 20:80) gave the desired product (27.65 g, 86%). MS $(M+NH_4)^+=277$.

(13b) A 2.5 M hexane solution of n-BuLi (42.8 mL, 1.02 eq) was added to diisopropylamine (15.0 mL, 1.02 eq) in THF (350 mL) at −78° C. The mixture was stirred at 0° C. for 15 min and cooled to −78° C. The acyl oxazolidinone from (13a) (27.15 g, 105 mmol) in THF (50 mL) was added dropwise. After 30 min at −78° C., t-butyl bromoacetate (22.52 g, 1.1 eq) in THF (50 mL) was added dropwise. After 30 min at −78° C., the cold bath was removed and the mixture was stirred at ambient temperature for 1.5 h, and quenched with saturated $NH_4Cl$ (300 mL). After removal of THF in vacuo, the residue was extracted with ethyl acetate (3×200 mL). The combined extracts were dried ($MgSO_4$) and concentrated. Silica gel column chromatography (ethyl acetate-hexane, 10:90 then 12.5:87.5 then 15:85) provided the desired product (24.95 g, 64%). MS $(M+Na)^+=396$.

(13c) Ozone was bubbled through a solution of the olefin from (12b) (12.9 g, 33.2 mmol) in dichloromethane (400 mL) at −78° C. until starting material disappeared as judged by TLC. The mixture was purged with nitrogen and treated with triphenylphosphine (10.5 g, 1.2 eq). After 4 h at ambient temperature, the mixture was concentrated in vacuo and purified by silica gel column chromatography (ethyl acetate-hexane, 30:70 then 40:60) to give the desired aldehyde (10.8 g, 87%). MS found: $(M+Na)^+=398$.

(13d) A mixture of the aldehyde from (13c) (10.4 g, 27.7 mmol), 4-benzyloxyaniline (5.52 g, 1 eq), sodium triacetoxyborohydride (7.63 g, 1.3 eq) in 1,2-dichloroethane (200 mL) was stirred at rt for 1.5 h. Following addition of saturated NaHCO$_3$ (20 mL) and ethyl acetate (500 mL), the mixture was washed with water (10 mL), brine (10 mL), dried (MgSO$_4$) and concentrated. The crude material was used in the next step without purification. MS found: (M+H)$^+$=559.

(13e) The crude material from (13d) was dissolved in toluene (300 mL), heated at reflux for 3 h, and concentrated. Silica gel column chromatography (ethyl acetate-hexane, 20:80 then 30:70) provided the desired lactam (6.30 g, 60% for 2 steps). MS (M+H)$^+$=382.

(13f) TFA (10 mL) was added to the t-butyl ester from (13e) (4.23 g, 11.1 mmol) in dichloromethane (40 mL) at 0° C. The solution was stirred at rt for 2 h and concentrated to give the desired carboxylic acid (4.03 g, 100%). MS (M+H)$^+$=326.

(13g) Following procedure similar to that described in step (13a), the carboxylic acid from (13f) (4.03 g, 11.1 mmol) was coupled with (R)-4-benzyloxazolidinone. Silica gel column chromatography (ethyl acetate-hexane, 40:60) provided the desired acyl oxazolidinone (4.50 g, 83%). MS (M+H)$^+$=485.

(13h) A 1 M THF solution of NaHMDS (0.40 mL) was added to the acyl oxazolidinone from (13g) (200 mg, 0.413 mmol) in THF (5 mL) at −78° C. After 1 h at this temperature, iodomethane (0.028 mL, 1.1 eq) added. The mixture was stirred at −78° C. for 1 h and at −20° C. for 6 h, and quenched with saturated NH$_4$Cl (3 mL). Following addition of ethyl acetate (100 mL), the mixture was washed with water (3 mL) and brine (3 mL), dried (MgSO$_4$) and concentrated. Silica gel column chromatography (ethyl acetate-hexane, 30:70 then 40:60) provided the methylated product as a 4:1 mixture of two isomers (65 mg, 32%). MS (M+H)$^+$=499.

(13i) The lactam from (13h) (160 mg, 0.321 mmol) and 20% palladium hydroxide on carbon (50 mg) in methanol (10 mL) and dichloromethane (5 mL) were stirred under balloon pressure hydrogen for 2 h. Following removal of catalyst by filtration, the filtrate was concentrated and purified by silica gel chromatography (ethyl acetate-hexane, 40:60 then 50:50) to give the less polar isomer (85 mg, 65%) and the more polar isomer (21 mg, 16%). MS found: (M+H)$^+$=409.

(13j–k) Following procedures analogous to steps (1f) and (1i), the less polar isomer from (13i) was converted to the title compound. The product was purified by reverse phase HPLC on a Dynamax-60A C-18 column eluting an acetonitrile:water:TFA gradient, to give the hydroxamic acid product. MS found: (M+H)$^+$=420.

Example 14

(2S)-N-Hydroxy-2-((3R)-1-{4-[(2-methyl-4-quinolinyl)methoxy]phenyl}-2-oxopyrrolidinyl) propanamide mono(Trifluoroacetate)

(14a–b) Following procedures analogous to steps (1f) and (1i), the more polar isomer from (13i) was converted to the title compound. The product was purified by reverse phase HPLC on a Dynamax-60A C-18 column eluting an acetonitrile:water:TFA gradient, to give the hydroxamic acid product. MS found: (M+H)$^+$=420.

Example 15

(2R)-N-hydroxy-2-((3R)-1-{4-[(2-methyl-4-quinolinyl)methoxy]phenyl}-2-oxopyrrolidinyl) pentanamide mono(Trifluoroacetate)

(15a–b) Following procedures analogous to steps (13h–i), (1f) and (1i), the acyl oxazolidinone from (13g) was reacted with allyl bromide and converted to the title compound. The product was purified by reverse phase HPLC on a Dynamax-60A C-18 column eluting an acetonitrile:water:TFA gradient, to give the hydroxamic acid product. MS found: (M+H)$^+$=448.

Example 16

(2S)-N,2-Dihydroxy-2-((3R)-1-{4-[(2-methyl-4-quinolinyl)methoxy]phenyl}-2-oxopyrrolidinyl) ethanamide mono(Trifluoroacetate)

(16a) A 2.5 M hexane solution of n-BuLi (125 mL, 2.1 eq) was added to diisopropylamine (45.8 mL, 2.2 eq) in THF (450 mL) at −78° C. The mixture was stirred at 0° C. for 30 min and cooled to −78° C. A mixture of dimethyl (S)-malate (24.1 g, 0.148 mol) and HMPA (27.2 mL, 1.05 eq) was added dropwise. The mixture was stirred at −78° C. for 30 min, at −20° C. for 30 min and then cooled to −78° C. Allyl bromide (16.7 mL, 1.5 eq) was added dropwise. The mixture was stirred at −78° C. for 30 min, −20° C. for 1 h and 0° C. for 1 h, then quenched with 10% citric acid until pH 7. Following removal of THF, the aqueous residue was extracted with ethyl acetate (3×300 mL). The combined extracts were washed with water (2×30 mL), brine (30 mL), dried (MgSO$_4$) and concentrated. Silica gel column chromatography (ethyl acetate-hexane, 30:70) provided the allylated product (19.6 g, 65%). $^1$H NMR analysis indicated the anti:syn ratio is 15:1. MS (M+H)$^+$=203.

(16b) NaH (3.46 g, 1 eq, 60% in mineral oil) was added to the alcohol from (16a) (17.5 g, 86.5 mmol) and benzyl bromide (20.6 mL, 2 eq) in DMF (260 mL) at 0° C. After 1 h at this temperature, the reaction mixture was quenched be careful addition of saturated NH$_4$Cl (300 mL). Most of the water and DMF were removed in vacuo. The residue was diluted with ethyl acetate (600 mL), washed with water (2×30 mL), brine (30 mL), dried (MgSO$_4$) and concentrated. Silica gel column chromatography (ethyl acetate-hexane, 10:90) provided the benzyl ether (13.0 g, 51%). MS (M+H)$^+$=293.

(16c) Following procedure analogous to step (1c), the olefin from (16b) (12.6 g, 43.1 mmol) was degraded via ozonolysis. Silica gel column chromatography (ethyl acetate-hexane, 10:90) provided the aldehyde (11.0 g, 86%). MS (M+H)$^+$=295.

(16d) Zinc dust (6.67 g, 10 eq) was added to a mixture of the aldehyde from (16c) (3.00 g, 10.2 mmol) and 4-benzyloxyaniline (2.03 g, 1 eq) in acetic acid (80 mL). The mixture was heated at reflux for 3 h and cooled to room temperature. The mixture was filtered and the filtrate concentrated. Silica gel column chromatography (ethyl acetate-hexane, 30:70) provided the lactam (460 mg, 10%). MS (M+H)$^+$=446.

(16e–g) Following procedures analogous to steps (1e–f) and (1i), the lactam from (16d) was converted to the title compound. The product was purified by reverse phase HPLC on a Dynamax-60A C-18 column eluting an acetonitrile:water:TFA gradient, to give the hydroxamic acid product. MS found: (M+H)$^+$=422.

Example 17

(1S)-1-{(3R)-1-[4-(Benzyloxy)phenyl]-2-oxopyrrolidinyl}ethyl(hydroxy)formamide (17a) Following procedures analogous to step (16a), methyl (R)-3-hydroxybutyrate (10.00 mL, 89.3 mmol) was reacted with allyl bromide. Silica gel column chromatography (ethyl acetate-hexane, 20:80 then 30:70 then 50:50) provided the anti product (4.24 g, 30%).

(17b) A 2 M hexane solution of Me3Al (74.1 mL, 6 eq) was slowly added to a solution of O-t-butylhydroxylamine hydrochloride (18.61 g, 6 eq) in dichloromethane (300 mL) at 0° C. After 15 min at rt, the ester from (17a) (3.90 g, 24.7 mmol) in THF (20 mL) was added. After 16 h at rt and 6 h at reflux, the mixture was quenched with 1 N HCl (100 mL) and water (100 mL). The two phases were separated and the aqueous phase extracted with dichloromethane (2×100 mL). The organic extracts were combined and washed with 1 N HCl (20 mL), brine (20 mL), dried ($MgSO_4$) and concentrated. Silica gel column chromatography (ethyl acetate-hexane, 50:50 then 80:20) provided the amide (2.50 g, 47%). MS $(M+H)^+$=216.

(17c) DEAD (5.01 mL, 3 eq) was added to a solution of the amide from (17b) (2.29 g, 10.6 mmol) and PPh3 (8.34 g, 3 eq) in THF (200 mL) at 0° C. After 20 h at rt, the mixture was quenched with saturated ammonium chloride (200 mL). After removal of THF in vacuo, the aqueous residue was extracted with ethyl acetate (3×100 mL). The extracts were washed with brine (20 mL), dried ($MgSO_4$) and concentrated. Silica gel column chromatography (ethyl acetate-hexane, 10:90 then 20:80) provided the β-lactam (1.40 g, 67%). MS $(M+H)^+$=198.

(17d) Following procedure analogous to step (1c), the olefin from (17c) (1.33 g, 6.74 mmol) was degraded via ozonolysis. Silica gel column chromatography (ethyl acetate-hexane, 50:50) provided the aldehyde (1.09 g, 81%). MS $(M+H)^+$=200.

(17e–f) Following procedure analogous to step (13d–e), the aldehyde from (17d) (713 mg, 3.58 mmol) was coupled with 4-benzyloxyaniline and cyclized. Silica gel column chromatography (ethyl acetate-hexane, 50:50) provided the y-lactam (850 mg, 62% for two steps). MS $(M+H)^+$=383.

(17g) Formic acetic anhydride (0.8 mL) was added to the amine from (17f) (700 mg, 1.83 mmol) in pyridine (3 mL) at 0° C. The mixture was stirred at 0° C. for 30 min and at rt for 3 h, heated at reflux for 3 h, and concentrated in vacuo. The residue was diluted with ethyl acetate (100 mL), washed with 1 N HCl (2 mL), water (2 mL) and brine (3 mL), dried ($MgSO_4$), and concentrated. Silica gel column chromatography (ethyl acetate-hexane, 40:60 then 50:50) provided the formamide (400 mg, 53%). MS $(M+H)^+$=411.

(17h) The formamide from (17g) (8 mg, 0.0195 mmol) was stirred in TFA (0.5 mL) and dichloromethane (2 mL) fro 1 h then concentrated to give the desired hydroxamic acid (4.5 mg, 65%). MS $(M+H)^+$=355.

Example 18

Hydroxy[(1S)-1-((3R)-1-{4-[(2-methyl-4-quinolinyl) methoxy]phenyl}-2-oxopyrrolidinyl)ethyl] formamide mono(Trifluoroacetate)

(18a–c) Following procedures analogous to steps (1e–f) and (17h), the formamide from (17g) was converted to the title compound. MS $(M+H)^+$=420.

Example 19

(2R,S)-((3SR)-3-Amino-1-{4-[2-methyl-4-quinolinyl)methoxy]phenyl)-2-oxopyrrolidinyl)-N-hydroxypentanamide (19a) To a solution of N-Boc-L-aspartic acid O-benzyl ester (40 g, 0.124 mol) in DMF (400 mL) was added potassium carbonate (51.3 g, 0.37 mol) followed by iodomethane (38.5 mL, 0.62 mol). The mixture was stirred at room temperature overnight and filtered. DMF was removed by concentration in vacuo. The residue was taken up in EtOAc and the solution was washed with brine, dried ($MgSO_4$) and concentrated to give a solid. Recrystallization from ether gave the α-methyl ester product (40 g, 95%) as a crystal. ESI $(M+Na)^+$=360.2.

(19b) The methyl ester (40 g, 0.119 mol) was dissolved in methanol (800 mL) in a 2000-mL flask. After addition of 10% Pd/C (5 g), hydrogen was bubbled into the solution for 2 hours. The catalyst was filtered off and the solution was concentrated in vacuo to give the β-carboxylic acid product (28.2 g, 96%) as a powder. ESI $(M+H)^+$=247.2.

(19c) To a solution of diisopropylamine (30.0 mL, 0.211 mol) in THF (250 mL) cooled to −78° C. was added 2.5 M n-butyllithium (82 mL, 0.205 mol). The mixture was stirred at 0° C. for 30 min and cooled back to −78° C. This solution was added to a solution of the β-carboxylic acid (15.8 g, 0.064 mol) in THF (300 mL) and the mixture was stirred at the same temperature for 1 hour. Allyl bromide (8.5 g, 0.070 mol) was added and the mixture was stirred in an ice bath for 5 hours, acidified with 10% citric acid to pH=3 and diluted with brine. The organic layer was separated and the aqueous layer was extracted with EtOAc two times. The combined organic phase was washed with brine, dried ($MgSO_4$) and concentrated. The residue was taken up in DMF (100 mL) and potassium carbonate (26.5 g, 0.192 mol) and iodomethane (19.4 mL, 0.32 mol) were added. The mixture was stirred at 50° C. for 2 hours. Insoluble material was filtered off and DMF was removed by concentration on a rotary evaporator in vacuo. The residue was taken up in EtOAc (300 mL) and the solution was washed with brine, dried ($MgSO_4$) and concentrated. Purification on a silica gel column (15% EtOAc/hexane) afforded N-Boc-α-allylaspartic acid dimethyl ester (12.5 g, 65%) as a powder. ESI $(M+Na)^+$=324.2.

(19d) Into a solution of the olefin 19c (12.5 g, 0.041 mol) in methylene chloride (150 mL) cooled to −78° C. was sequentially bubbled O2 for 10 min, O3 for 30 min and $N_2$. Once the blue color dissipated, trimethylphosphine (10.3 g, 0.083 mol) was added. The solution was allowed to stir at room temperature overnight, washed with brine, dried ($MgSO_4$) and concentrated. Chromatography on a silica gel column (30% EtOAc/hexane) afforded the aldehyde (10.5 g, 85%) as an oil. ESI $(M+H)^+$=304.1.

(19e) A solution of the aldehyde (10.3 g, 0.034 mol) and 4-benzyloxyaniline (6.7 g, 0.034 mol) in toluene (250 mL) was stirred at reflux for 8 hours and the solvent was removed in vacuo. The residue was taken up in dichloroethane (200 mL) and sodium triacetoxyborohydride (9.3 g, 0.044 mol) was added. The mixture was stirred at room temperature overnight and concentrated. EtOAc (400 mL) was added followed by aqueous $NaHCO_3$. The organic phase was washed with $NaHCO_3$ and brine, dried ($MgSO_4$) and concentrated. The residue was taken up in toluene (200 mL) and the solution was stirred at reflux for 48 hours and concentrated. The residue was purified on a silica gel column (35% EtOAc/hexane) to give the lactam (6.67 g, 43%) as a solid. ESI $(M+H)^+$=455.2.

(19f) To a solution of the lactam (6.12 g, 0.0135 mol) in THF (30 mL) at −78° C. was added a LDA solution (0.031 mol) in THF (15 mL) prepared as described in (1c). The mixture was stirred at −78° C. for 30 min and at 0° C. for 30 min. After cooling back to −78° C., allyl bromide (1.3 mL, 0.015 mol) was added. The solution was stirred at 0°

C. for 4 hours and at room temperature for 1 hour. The reaction was quenched with 10% citric acid. EtOAc was added and the solution was washed with brine, dried (MgSO$_4$) and concentrated. Purification on a silica gel column (25% EtOAc/hexane) afforded the olefin product (2.4 g, 36%) as a powder. ESI (M+H)$^+$=495.3.

(19g) The olefin product (2.29 g, 46.3 mmol) was dissolved in methanol (50 mL) and 10% Pd-C (500 mg) was added. The mixture was hydrogenated at 1 atmospheric pressure for 3 hours. The catalyst was filtered off and the solution was concentrated to give the phenol derivative (1.81 g, 96%) as a powder. ESI (M+H)$^+$=407.1.

(19h) To a solution of the phenol derivative (1.81 g, 44.6 mmol) in DMSO (10 mL) were added cesium carbonate (1.88 g, 58 mmol), tetrabutylammonium iodide (1.81 g, 49 mmol) and 4-chloromethyl-2-methylquinoline (1.1 g, 57.9 mmol) in sequence. The mixture was stirred at 60° C. overnight. EtOAc was added and the solution was washed with brine, dried (MgSO$_4$) and concentrated. Chromatography on a silica gel column (50% EtOAC/hexane) gave the quinoline derivative (2.24 g, 90%) as a powder. ESI (M−H)$^−$=560.3.

(19i) The quinoline derivative (2.06 g, 36.7 mmol) was dissolved in 4 N HCl in dioxane (60 mL). The solution was stirred at room temperature for 2 hours and concentrated to give the deprotection product as a solid. ESI (M+H)$^+$=462.2.

(19j) A solution of 19i (1.95 g, 36.5 mmol) in MeOH (30 mL) and 1 N KOH (25 mL) was stirred at 60° C. for 8 hours and concentrated. The residue was acidified with 1 N HCl to pH=7 and EtOAc (100 mL) was added. The solution was dried (MgSO$_4$) and concentrated to give the carboxylic acid (1.39 g, 85%) as a solid. ESI (M+H)$^+$= 448.2.

(19k) To a solution of the carboxylic acid (100 mg, 0.22 mmol) in DMF (2 mL) cooled in an ice bath was added a solution of hydroxylamine hydrochloride (14 mg, 2 mmol) in DMF (0.5 mL) and diisopropylethylamine (390 mg, 3 mmol) followed by BOP (21 mg, 0.4 mmol). The mixture was stirred in the ice bath for 1 hour. Purification on reversed phase HPLC afforded the hydroxamic acid as a powder. ESI (M+H)$^+$=463.2.

Example 20

(2S,R)-((3S,R)-3-Amino-1-{4-[2-methyl-4-quinolinyl)methoxy]phenyl}-2-oxopyrrolidinyl)-N-hydroxypentanamide (20a) To a solution 19f (2.55 g, 5.16 mmol) in THF (50 mL) at −78° C. was added a LDA solution (11.8 mmol) in THF (8 mL) prepared as described in (1c). The solution was stirred in an ice bath for 1 hour and cooled back to −78° C. The reaction was quenched with MeOH. EtOAc was added and the solution was washed with brine, dried (MgSO$_4$) and concentrated. Purification on a silica gel column (35% EtOAc/hexane) gave a mixture of the epimerized product and the starting material with a ratio of 1:3.

(20b) The mixture was hydrogenated using a procedure similar to that described in (19g). ESI (M+H)$^+$=407.2.

(20c) The hydrogenated product was reacted with 4-chloromethyl-2-methylquinoline using a procedure similar to that described in (19h). ESI (M+H)$^+$=562.4.

(20d) The quinoline derivative was treated with 4 N HCl to remove the Boc group using a procedure similar to that described in (19i). ESI (M+H)$^+$=462.2.

(20e) The deprotected product was saponified using a procedure similar to that described in (19j). Separation of the two diastereomers on reversed phase HPLC gave the desired epimerized diastereomer as a powder. ESI (M+H)$^+$=448.2.

(20f) The carboxylic acid 20e was coupled with hydroxylamine hydrochloride using a procedure similar to that described in (19k) to give the hydroxamic acid. ESI (M+H)$^+$=463.2.

Example 21

(2S,R)-((3S,R)-3-Amino-1-{4-[2-methyl-4-quinolinyl)methoxy]phenyl}-2-oxopyrrolidinyl)-N-hydroxypropanamide (21a) To a solution of 19e (3 g, 6.6 mmol) in THF (60 mL) cooled to −78° C. was added a LDA solution (15 mmol) in THF (40 mL) prepared using the procedure described in (1f) and the solution was stirred at the same temperature for 1 hour. To it was added iodomethane (0.5 mL, 7.92 mmol) and the solution was stirred in an ice bath for 1 hour and at room temperature for another hour. The reaction was quenched with citric acid solution. EtOAc was added and the solution was washed with brine, dried (MgSO$_4$) and concentrated. Chromatography on a silica gel column (40% EtOAc/hexane) afforded the methylated product (1.9 g, 61%) as a solid. ESI (M+H)$^+$=469.2.

(21b) The methylated product was epimerized using a procedure described in (20a) to give a mixture of two diastereomers with a ratio of 1:1.

(21c) The mixture was hydrogenated using a procedure similar to that described in (19g) to give the phenol derivative. ESI (M+H)$^+$=379.2.

(21d) The phenol derivative was alkylated with 4-chloromethyl-2-quinoline using a procedure similar to that described in (19h). ESI (M+H)$^+$=534.2.

(21e) The quinoline derivative was treated with an acid using the procedure described in (19i). ESI (M+H)$^+$= 434.1.

(21f) The deprotected product was saponified using the procedure described in (19j). The desired epimerized diastereomer was isolated using reversed phase HPLC. ESI (M+H)$^+$=420.3.

(21g) Coupling of the carboxylic acid with hydroxylamine using the procedure described in (19k) afforded the hydroxamic acid. ESI (M+H)$^+$=435.1.

Example 22

(2S,R)-((3S,R)-3-(Dimethylamino)-1-{4-[2-methyl-4-quinolinyl)methoxy]phenyl}-2-oxopyrrolidinyl)-N-hydroxypropanamide (22a) The intermediate 21e (400 mg, 0.6 mmol) was dissolved in MeOH (20 mL) and diisopropylethylamine (0.41 mL, 3 mmol), formaldehyde (37% solution in water, 0.55 mL, 1.8 mmol) and NaBH$_3$CN (95 mg, 1.5 mmol) were added. The mixture was stirred at room temperature overnight. More formaldehyde (0.55 mL) and NaBH$_3$CN (95 mg) were added and the mixture was stirred another overnight and concentrated. The residue was taken up in EtOAc and the solution was washed with brine, dried (MgSO$_4$) and concentrated. ESI (M+H)$^+$=462.2.

(22b) The intermediate 22a (245 mg, 0.53 mmol) was dissolved in MeOH and to it was added 1 N KOH (3 mL). The solution was stirred at reflux overnight and concentrated. The residue was acidified with aqueous TFA. Purification on reversed phase HPLC separated the two diastereomers. ESI (M+H)$^+$=448.2.

(22c) The carboxylic acid 22b was coupled with hydroxylamine hydrochloride using the procedure described in (1k) to give the hydroxamic acid. ESI (M+H)$^+$=463.2.

Example 23

2-((3S,R)-3-Amino-1-{4-[2-methyl-4-quinolinyl)methoxy]phenyl}-2-oxopyrrolidinyl)-N-hydroxyacetamide

This compound was prepared from the intermediate 1e by hydrogenation, alkylation with 4-chloromethyl-2-methylquinoline and saponification followed by coupling of the carboxylic acid with hydroxylamine using the procedures described in Example 19. ESI (M+H)$^+$=421.1.

TABLE 1

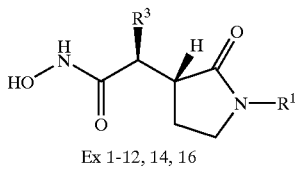

Ex 1-12, 14, 16

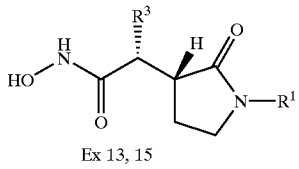

Ex 13, 15

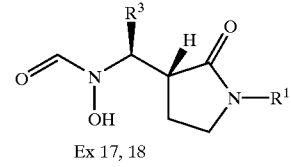

Ex 17, 18

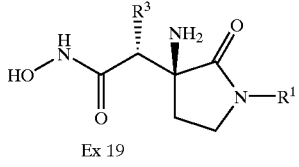

Ex 19

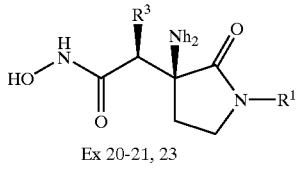

Ex 20-21, 23

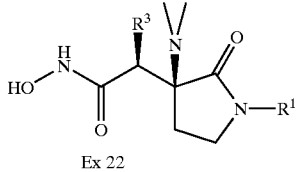

Ex 22

| Ex # | R$^1$ | R$^3$ | MS (M + H)$^+$ |
|---|---|---|---|
| 1 | 4-[(2-methyl-4-quinolinyl)methoxy]phenyl | (2,2-dimethyl-1-oxo-propyl)amino | 487 |
| 2 | 4-[(2-methyl-4-quinolinyl)methoxy]phenyl | [(1,1-dimethylethoxy)carbonyl]amino | 521 |
| 3 | 4-[(2-methyl-4-quinolinyl)methoxy]phenyl | amino | 421 |
| 4 | 4-[(2-methyl-4-quinolinyl)methoxy]phenyl | acetylamino | 463 |
| 5 | 4-[(2-methyl-4-quinolinyl)methoxy]phenyl | [(4-morpholinyl)carbonyl]amino | 534 |
| 6 | 4-[(2,6-dimethyl-4-pyridinyl)methoxy]phenyl | [(1,1-dimethylethoxy)carbonyl]amino | 485 |
| 7 | 4-[(2,6-dimethyl-4-pyridinyl)methoxy]phenyl | amino | 387 |
| 8 | 4-[(2-methyl-4-quinolinyl)methoxy]phenyl | (methoxycarbonyl)amino | 479 |
| 9 | 4-[(2-methyl-4-quinolinyl)methoxy]phenyl | (butoxycarbonyl)amino | 520 |
| 10 | 4-[(2-methyl-4-quinolinyl)methoxy]phenyl | (benzoyl)amino | 525 |
| 11 | 4-[(2-methyl-4-quinolinyl)methoxy]phenyl | 1-pyrrolyl | 471 |
| 12 | 4-[(2-methyl-4-quinolinyl)methoxy]phenyl | dimethylamino | 449 |
| 13 | 4-[(2-methyl-4-quinolinyl)methoxy]phenyl | methyl | 420 |
| 14 | 4-[(2-methyl-4-quinolinyl)methoxy]phenyl | methyl | 420 |
| 15 | 4-[(2-methyl-4-quinolinyl)methoxy]phenyl | propyl | 448 |
| 16 | 4-[(2-methyl-4-quinolinyl)methoxy]phenyl | hydroxy | 422 |
| 17 | 4-benzyloxyphenyl | methyl | 355 |
| 18 | 4-[(2-methyl-4-quinolinyl)methoxy]phenyl | methyl | 420 |
| 19 | 4-[(2-methyl-4-quinolinyl)methoxy]phenyl | propyl | 463 |
| 20 | 4-[(2-methyl-4-quinolinyl)methoxy]phenyl | propyl | 463 |
| 21 | 4-[(2-methyl-4-quinolinyl)methoxy]phenyl | methyl | 435 |
| 22 | 4-[(2-methyl-4-quinolinyl)methoxy]phenyl | methyl | 463 |
| 23 | 4-[(2-methyl-4-quinolinyl)methoxy]phenyl | H | 421 |

The following table contains representative examples of the present invention. Each entry in each table is intended to be paired with each formula at the start of the table. For example, example 1 is intended to be paired with each of formulae A1-JJ4.

TABLE 2

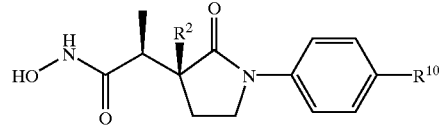

A1 (R$^2$ = H)
A2 (R$^2$ = Me)
A3 (R$^2$ = NH$_2$)
A4 (R$^2$ = OH)

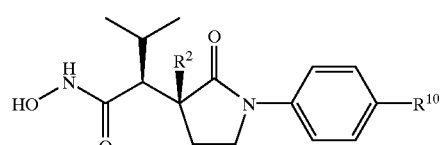

B1 (R$^2$ = H)
B2 (R$^2$ = Me)
B3 (R$^2$ = NH$_2$)
B4 (R$^2$ = OH)

TABLE 2-continued
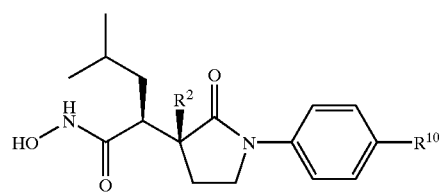
C1 (R² = H)
C2 (R² = Me)
C3 (R² = NH₂)
C4 (R² = OH)
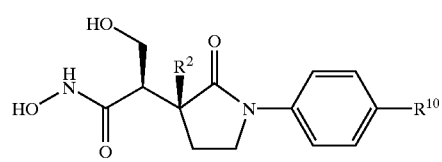
D1 (R² = H)
D2 (R² = Me)
D3 (R² = NH₂)
D4 (R² = OH)
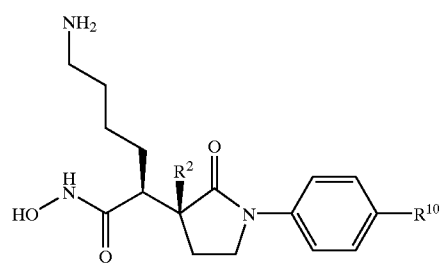
E1 (R² = H)
E2 (R² = Me)
E3 (R² = NH₂)
E4 (R² = OH)
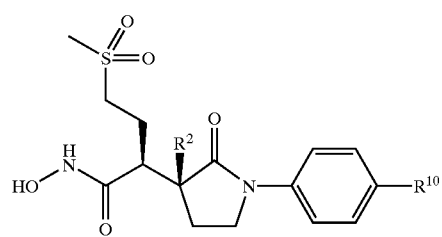
F1 (R² = H)
F2 (R² = Me)
F3 (R² = NH₂)
F4 (R² = OH)
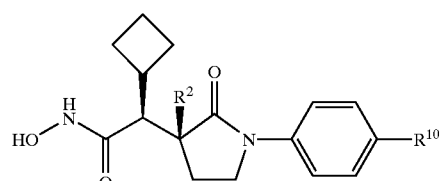
G1 (R² = H)
G2 (R² = Me)
G3 (R² = NH₂)
G4 (R² = OH)
TABLE 2-continued
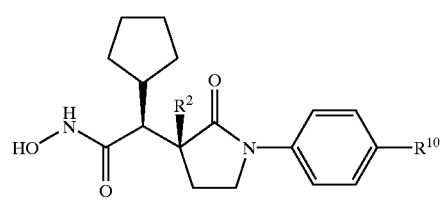
H1 (R² = H)
H2 (R² = Me)
H3 (R² = NH₂)
H4 (R² = OH)
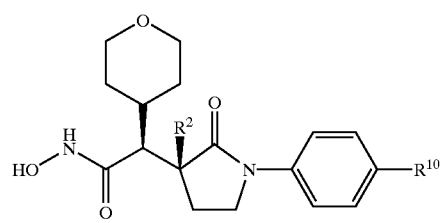
I1 (R² = H)
I2 (R² = Me)
I3 (R² = NH₂)
I4 (R² = OH)
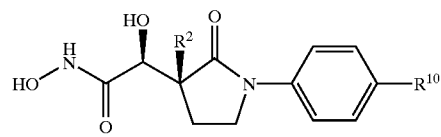
J1 (R² = H)
J2 (R² = Me)
J3 (R² = NH₂)
J4 (R² = OH)
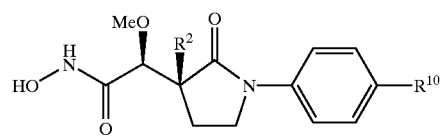
K1 (R² = H)
K2 (R² = Me)
K3 (R² = NH₂)
K4 (R² = OH)
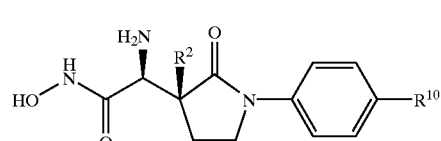
L1 (R² = H)
L2 (R² = Me)
L3 (R² = NH₂)
L4 (R² = OH)

TABLE 2-continued
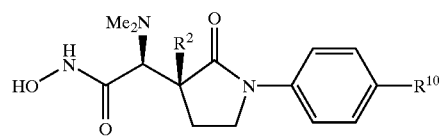
M1 (R² = H)
M2 (R² = Me)
M3 (R² = NH₂)
M4 (R² = OH)
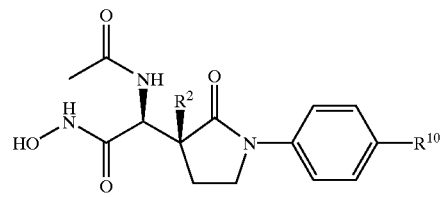
N1 (R² = H)
N2 (R² = Me)
N3 (R² = NH₂)
N4 (R² = OH)
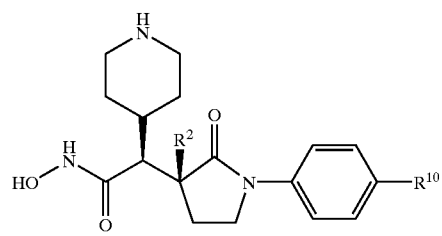
O1 (R² = H)
O2 (R² = Me)
O3 (R² = NH₂)
O4 (R² = OH)
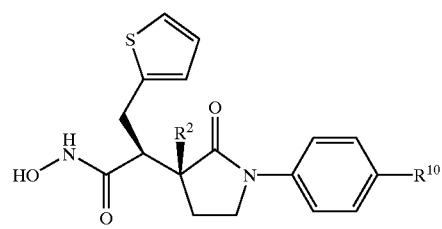
P1 (R² = H)
P2 (R² = Me)
P3 (R² = NH₂)
P4 (R² = OH)
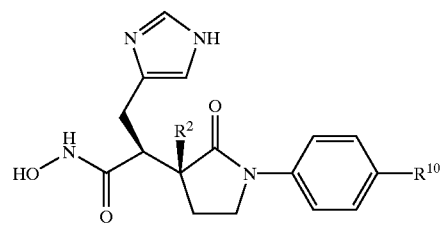
Q1 (R² = H)
Q2 (R² = Me)
Q3 (R² = NH₂)
Q4 (R² = OH)
TABLE 2-continued
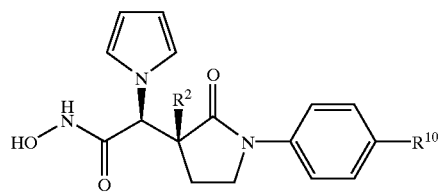
R1 (R² = H)
R2 (R² = Me)
R3 (R² = NH₂)
R4 (R² = OH)
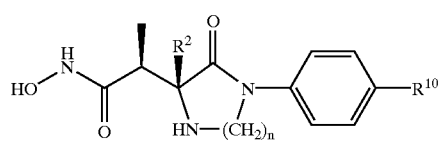
S1 (R² = H, n = 1)
S2 (R² = Me, n = 1)
S3 (R² = H, n = 2)
S4 (R² = Me, n = 2)
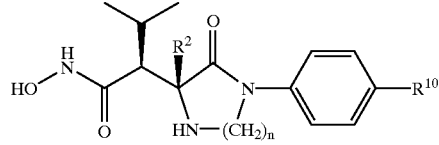
T1 (R² = H, n = 1)
T2 (R² = Me, n = 1)
T3 (R² = H, n = 2)
T4 (R² = Me, n = 2)
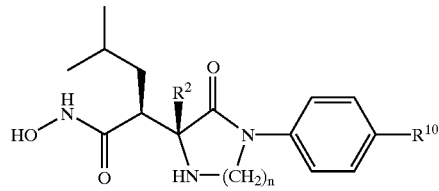
U1 (R² = H, n = 1)
U2 (R² = Me, n = 1)
U3 (R² = H, n = 2)
U4 (R² = Me, n = 2)
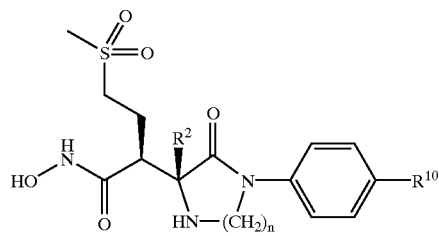
V1 (R² = H, n = 1)
V2 (R² = Me, n = 1)
V3 (R² = H, n = 2)
V4 (R² = Me, n = 2)

TABLE 2-continued

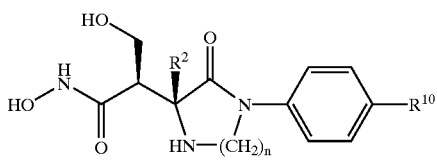

W1 (R$^2$ = H, n = 1)
W2 (R$^2$ = Me, n = 1)
W3 (R$^2$ = H, n = 2)
W4 (R$^2$ = Me, n = 2)

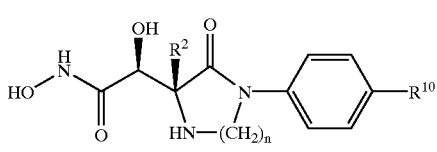

X1 (R$^2$ = H, n = 1)
X2 (R$^2$ = Me, n = 1)
X3 (R$^2$ = H, n = 2)
X4 (R$^2$ = Me, n = 2)

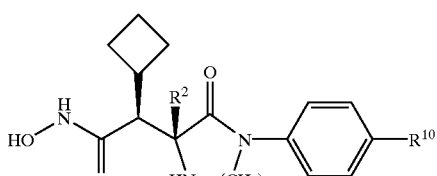

Y1 (R$^2$ = H, n = 1)
Y2 (R$^2$ = Me, n = 1)
Y3 (R$^2$ = H, n = 2)
Y4 (R$^2$ = Me, n = 2)

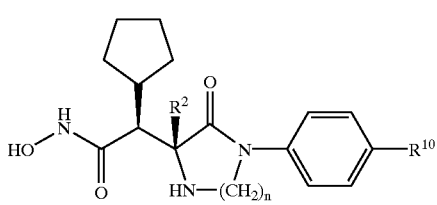

Z1 (R$^2$ = H, n = 1)
Z2 (R$^2$ = Me, n = 1)
Z3 (R$^2$ = H, n = 2)
Z4 (R$^2$ = Me, n = 2)

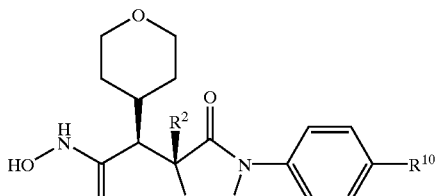

AA1 (R$^2$ = H, n = 1)
AA2 (R$^2$ = Me, n = 1)
AA3 (R$^2$ = H, n = 2)
AA4 (R$^2$ = Me, n = 2)

TABLE 2-continued

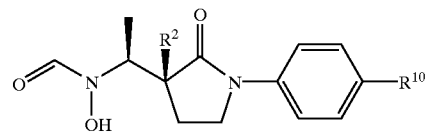

BB1 (R$^2$ = H)
BB2 (R$^2$ = Me)
BB3 (R$^2$ = NH$_2$)
BB4 (R$^2$ = OH)

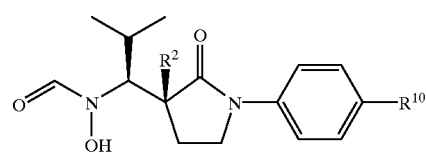

CC1 (R$^2$ = H)
CC2 (R$^2$ = Me)
CC3 (R$^2$ = NH$_2$)
CC4 (R$^2$ = OH)

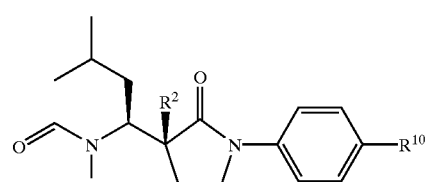

DD1 (R$^2$ = H)
DD2 (R$^2$ = Me)
DD3 (R$^2$ = NH$_2$)
DD4 (R$^2$ = OH)

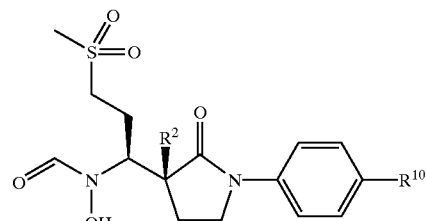

EE1 (R$^2$ = H)
EE2 (R$^2$ = Me)
EE3 (R$^2$ = NH$_2$)
EE4 (R$^2$ = OH)

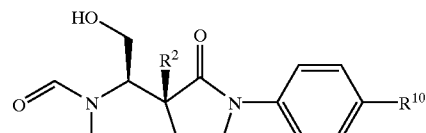

FF1 (R$^2$ = H)
FF2 (R$^2$ = Me)
FF3 (R$^2$ = NH$_2$)
FF4 (R$^2$ = OH)

TABLE 2-continued

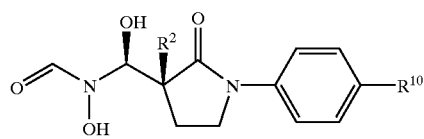

GG1 (R² = H)
GG2 (R² = Me)
GG3 (R² = NH₂)
GG4 (R² = OH)

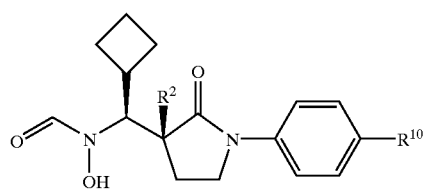

HH1 (R² = H)
HH2 (R² = Me)
HH3 (R² = NH₂)
HH4 (R² = OH)

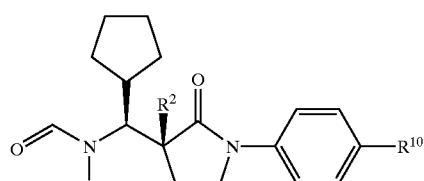

II1 (R² = H)
II2 (R² = Me)
II3 (R² = NH₂)
II4 (R² = OH)

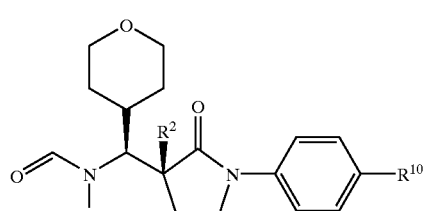

JJ1 (R² = H)
JJ2 (R² = Me)
JJ3 (R² = NH₂)
JJ4 (R² = OH)

| Ex # | R¹⁰ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |

UTILITY

The compounds of formula I are expected to possess matrix metalloproteinase and/or aggrecanase and/or TNF inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, *Cancer and Metastasis Reviews*, 1990, 9,289–303). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 μM for the inhibition of a desired MP. Preferred compounds of the present invention have $K_i$'s or $IC_{50}$'s of $\leq 1$ μM. More preferred compounds of the present invention have $K_i$'s or $IC_{50}$'s of $\leq 0.1$ μM. Even more preferred compounds of the present invention have $K_i$'s or $IC_{50}$'s of $\leq 0.01$ μM. Still more preferred compounds of the present invention have $K_i$'s or $IC_{50}$'s of $\leq 0.001$ μM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase, time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et. al. *Trans. Ortho. Res. Soc.* 1995, 20, 341). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 μM for aggrecanase.

To evaluate inhibition of aggrecanase, compounds are prepared as 10 mM stocks in DMSO, water or other solvents and diluted to appropriate concentrations in water. Drug (50 μl) is added to 50 μl of aggrecanase-containing media and 50 μl of 2 mg/ml aggrecan substrate and brought to a final volume of 200 μl in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody $BC_3$. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

MMP Screens

The enzymatic activities of recombinant MMP-1, 2, 3, 9, and 13 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the lactams studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2 \times 10^6$ cells/ml in 96 well polystyrene plates. Cells were preincubated 10 minutes with compound, then stimulated with 1 $\mu$g/ml LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 $\mu$M. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 mg of D-galactosamine plus 10 $\mu$g of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

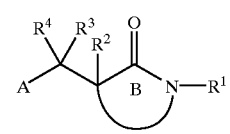

or a stereoisomer or pharmaceutically acceptable salt form thereof, wherein;

A is selected from —CONHOH, —C(RR')CONHOH, —CONHOR$^5$, —CONHOR$^6$, —N(OH)C(O)R$^5$, —SONHR$^a$, SN$_2$H$_2$R$^a$, PO(OH)$_2$, and PO(OH)NHR$^a$;

ring B is pyrrolidinone;

R$^1$ is U—X—Y—Z—U$^a$—X$^a$—Y$^a$—X$^b$—Z$^a$;

U is absent;

X is absent;

Y is absent;

Z is phenyl substituted with 0–5 R$^b$;

U$^a$ is absent or is selected from: O, NR$^a$, C(O), C(O)O, OC(O), C(O)NR$^a$, NR$^a$C(O), OC(O)O, OC(O)NR$^a$, NR$^a$C(O)O, NR$^a$C(O)NR$^a$, S(O)$_p$, S(O)$_p$NR$^a$, NR$^a$S(O)$_p$, and NR$^a$SO$_2$NR$^a$;

X$^a$ is absent or selected from C$_{1-10}$ alkylene, C$_{2-10}$ alkenylene, C$_{2-10}$ alkynylene;

$Y^a$ is absent or selected from O, $NR^a$, $S(O)_p$, and C(O);
$X^b$ is absent or selected from $C_{1-10}$ alkylene, $C_{2-10}$ alkenylene, $C_{2-10}$ alkynylene;
$Z^a$ is selected from H, a $C_{3-13}$ carbocycle substituted with 0–5 $R^c$ and a 5–14 membered heterocyclic system containing from 1–4 heteroatoms selected from the group consisting of N, O, and S and substituted with 0–5 $R^c$;
$R^2$ is selected from H, Q', $C_{1-10}$ alkylene-Q', $C_{2-10}$ alkenylene-Q', $C_{2-10}$ alkynylene-Q', $(CRR')_rO(CRR')_r$—Q', $(CRR')_rNR^a(CRR')_r$—Q', $(CRR')_rNR^aC(O)(CRR')_r$—Q', $(CRR')_rC(O)NR^a(CRR')_r$—Q', $(CRR')_rC(O)(CRR')_r$—Q', $(CRR')_rC(O)O(CRR')_r$—Q', $(CRR')_rS(O)_p(CRR')_r$—Q, $(CRR')_rSO_2NR^a(CRR')_r$—Q', $(CRR')_rNR^aC(O)NR^a(CRR')_r$—Q', $(CRR')_rOC(O)NR^a(CRR')_r$—Q', and $(CRR')_rNR^aC(O)O(CRR')_r$—Q';
R, at each occurrence, is independently selected from H, $CH_3$, $CH_2CH_3$, $CH(CH_3)_2$, $CH=CH_2$, $CH=CHCH_3$, and $CH_2CH=CH_2$;
R', at each occurrence, is independently selected from H, $CH_3$, $CH_2CH_3$, and $CH(CH_3)_2$;
Q' is selected from H, a $C_{3-13}$ carbocycle substituted with 0–5 $R^b$ and a 5–14 membered heterocyclic system containing from 1–4 heteroatoms selected from the group consisting of N, O, and S and substituted with 0–5 $R^b$;
$R^3$ is selected from H, Q, $C_{1-10}$ alkylene-Q', $C_{2-10}$ alkenylene-Q, $C_{2-10}$ alkynylene-Q', $(CRR')_rO(CRR')_r$—Q, $(CRR')_rNR^a(CRR')_r$—Q, $(CRR')_rNR^aC(O)(CRR')_r$—Q, $(CRR')_rC(O)O(CRR')r$—Q, $(CRR')_rOC(O)(CRR')_r$—Q, $(CRR')_rNR^aC(O)NR^a(CRR')_r$—Q, $(CRR')_rNR^aC(O)(CRR')_r$—Q, $(CRR')_rNR^aOC(O)O(CRR')_r$—Q, $(CRR')_rNR^aOC(O)NR^a(CRR')_r$—Q, $(CRR')_rNR^aC(O)O(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a(CRR')_r$—Q, $(CRR')_rNR^aC(O)(CRR')_{r''}$—NHQ, $(CRR')_rNR^aC(O)(CRR')_rNHC(O)OR^a$, and $(CRR')_rNR^aC(O)(CRR')_rNHC(O)(CRR')_rNHC(O)OR^a$,
Q is selected from H, a $C_{3-13}$ carbocycle substituted with 0–5 $R^b$ and a 5–14 membered heterocyclic system containing from 1–4 heteroatoms selected from the group consisting of N, O, and S and substituted with 0–5 $R^b$;
$R^4$ is selected from H, $C_{1-10}$ alkylene-H, $C_{2-10}$ alkenylene-H, $C_{2-10}$ alkynylene-H, $(CRR')_rO(CRR')_r$—H, $(CRR')_rNR^a(CRR')_r$—H, $(CRR')_rC(O)(CRR')_r$—H, $(CRR')_rC(O)O(CRR')_r$—H, $(CRR')_rOC(O)(CRR')_r$—H, $(CRR')_rC(O)NR^a(CRR')_r$—H, $(CRR')_rNR^aC(O)(CRR')_r$—H, $(CRR')_rOC(O)O(CRR')_r$—H, $(CRR')_rOC(O)NR^a(CRR')_r$—H, $(CRR')_rNR^aC(O)O(CRR')_r$—H, $(CRR')_rNR^aC(O)NR^a(CRR')_r$—H, $(CRR')_rS(O)_p(CRR')_r$—H, $(CRR')_rSO_2NR^a(CRR')_r$—H, $(CRR')_rR^aSO_2(CRR')_r$—H, and $(CRR')_rNR^aSO_2NR^a(CRR')_r$—H;
alternatively, $R^3$ and $R^4$ combine to form a $C_{3-13}$ carbocycle substituted with $R^c$ and 0–3 $R^b$ or a 5–14 membered heterocyclic system containing from 1–4 heteroatoms selected from the group consisting of N, O, and S and substituted with $R^c$ and 0–3 $R^b$;
$R^a$, at each occurrence, is independently selected from H, $C_{1-4}$ alkyl, phenyl and benzyl;
$R^{a'}$, at each occurrence, is independently selected from H, $C_{1-4}$ alkyl, phenyl and benzyl;
$R^{a''}$, at each occurrence, is independently selected from H, $C_{1-4}$ alkyl, benzyl, $C_{3-7}$ carbocycle, or a 5 to 6 membered heteroaromatic ring containing 1–4 heteroatoms selected from the group consisting of N, O, and S;
alternatively, $R^a$ and $R^{a'}$ taken together with the nitrogen to which they are attached form a 4, 5, or 6 membered ring containing from 0–1 additional heteroatoms selected from the group consisting of N, O, and S;
$R^b$, at each occurrence, is independently selected from $C_{1-6}$ alkyl, $OR^a$, Cl, F, Br, I, =O, CN, $NO_2$, $NR^aR^{a'}$, $C(O)R^{a''}$, $C(O)OR^a$, $C(O)NR^aR^{a'}$, $S(O)_2NR^aR^{a'}$, $S(O)_pR^a$, $CF_3$, and $CF_2CF_3$;
$R^c$, at each occurrence, is independently selected from $C_{1-6}$ alkyl, $OR^a$, Cl, F, Br, I, =O, CN, $NO_2$, $NR^aR^{a'}$, $C(O)R^{a''}$, $C(O)OR^a$, $C(O)NR^aR^{a'}$, $NR^aC(O)NR^aR^{a'}$, $S(O)_2NR^aR^{a'}$, $S(O)_pR^a$, $CF_3$, $CF_2CF_3$, —CH(=NOH), —C(=NOH)$CH_3$, $(CRR')_sO(CRR')_sR^d$, $(CRR')_sS(O)_p(CRR')_sR^d$, $(CRR')_sNR^a(CRR')_sR^d$phenyl, and a 5–14 membered heterocyclic system containing from 1–4 heteroatoms selected from the group consisting of N, O, and S;
$R^5$, at each occurrence, is selected from H, $C_{1-10}$ alkyl substituted with 0–2 $R^b$, and $C_{1-8}$ alkyl substituted with 0–2 $R^d$;
$R^d$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system containing from 1–4 heteroatoms selected from the group consisting of N, O, and S and substituted with 0–3 $R^b$;
$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_{1-5}$ alkyl)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, —CH($R^8$)OC(=O)$OR^9$, and

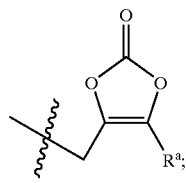

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;
$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;
$R^8$ is selected from H and $C_{1-4}$ linear alkyl;
$R^9$ is selected from H, $C_{1-8}$ alkyl substituted with 1–2 $R^e$, $C_{3-8}$ cycloalkyl substituted with 1–2 $R^e$, and phenyl substituted with 0–2 $R^b$;
$R^e$, at each occurrence, is selected from $C_{1-4}$ alkyl, $C_{3-8}$ cycloalkyl, $C_{1-5}$ alkoxy, phenyl substituted with 0–2 $R^b$;
p, at each occurrence, is selected from 0, 1, and 2;
r, at each occurrence, is selected from 0, 1, 2, 3, 4, and 5;

r', at each occurrence, is selected from 0, 1, 2, 3, 4, and 5;

r", at each occurrence, is selected from 1, 2, and 3;

s, at each occurrence, is selected from 0, 1, 2, and 3; and, s', at each occurrence, is selected from 0, 1, 2, and 3.

2. A compound according to claim 1, wherein;

A is selected from —CONHOH, CH(R)CONHOH, —CONHOR$^5$, —CONHOR$^6$, and —N(OH)COR$^5$;

U$^a$ is absent or is selected from: O, NR$^a$, C(O), C(O)NR$^a$, NR$^a$C(O), OC(O)NR$^a$, NR$^a$C(O)O, NR$^a$C(O)NR$^a$, S(O)$_p$NR$^a$, and NR$^a$S(O)$_p$;

R$^2$ is selected from H, Q', C$_{1-5}$ alkylene-Q', C$_{2-5}$ alkenylene-Q', C$_{2-5}$ alkynylene-Q', (CRR')$_r$O(CRR')$_r$—Q', (CRR')$_r$NR$^a$(CRR')$_r$—Q', (CRR')$_r$NR$^a$C(O)(CRR')$_r$—Q', (CRR')$_r$C(O)NR$^a$(CRR')$_r$—Q', (CRR')$_r$NR$^a$C(O)NR$^a$(CRR')$_r$—Q', (CRR')$_r$C(O)(CRR')$_r$—Q', (CRR')$_r$C(O)O(CRR')$_r$—Q', (CRR')$_r$S(O)$_p$(CRR')$_r$—Q', and (CRR')$_r$SO$_2$NR$^a$(CRR')$_r$—Q';

Q' is selected from H, phenyl substituted with 0–3 R$^b$ and a 5–6 membered heteroaryl system containing from 1–4 heteroatoms selected from the group consisting of N, O, and S and substituted with 0–3 R$^b$;

R$^3$ is selected from H, Q, C$_{1-10}$ alkylene-Q, C$_{2-10}$ alkenylene-Q, C$_{2-10}$ alkynylene-Q, (CRR')$_r$O(CRR')$_r$—Q, (CRR')$_r$NR$^a$(CRR')$_r$—Q, (CRR')$_r$C(O)(CRR')$_r$—Q, (CRR')$_r$C(O)NR$^a$(CRR')$_r$—Q, (CRR')$_r$NR$^a$C(O)(CRR')$_r$—Q, (CRR')$_r$OC(O)NR$^a$(CRR')$_r$—Q, (CRR')$_r$NR$^a$C(O)O(CRR')$_r$—Q, (CRR')$_r$NR$^a$C(O)NR$^a$(CRR')$_r$—Q, (CRR')$_r$S(O)$_p$(CRR')$_r$—Q, (CRR')$_r$ SO$_2$NR$^a$(CRR')$_r$—Q, (CRR')$_r$NR$^a$SO$_2$(CRR')$_r$—Q, and (CRR')$_r$NR$^a$SO$_2$NR$^a$(CRR')$_r$—Q';

R, at each occurrence, is independently selected from H, CH$_3$, and CH$_2$CH$_3$;

R', at each occurrence, is independently selected from H and CH$_3$;

Q is selected from H, a C$_{3-10}$ carbocycle substituted with 0–5 R$^b$ and a 5–10 membered heterocyclic system containing from 1–4 heteroatoms selected from the group consisting of N, O, and S and substituted with 0–5 R$^b$; and, R$^c$, at each occurrence, is independently selected from C$_{1-6}$ alkyl, OR$^a$, Cl, F, Br, I, =O, CN, NO$_2$, NR$^a$R$^{a'}$, C(O)R$^{a''}$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–10 membered heterocyclic system containing from 1–4 heteroatoms selected from the group consisting of N, O, and S.

3. A compound according to claim 2, wherein;

A is selected from —CONHOH, CH(R)CONHOH, —CONHOR$^5$, and —N(OH)COR$^5$;

Z is phenyl;

U$^a$ is absent or is selected from: O, NR$^a$, C(O), C(O)NR$^a$, NR$^a$C(O), and S(O)$_p$NR$^a$;

X$^a$ is absent or C$_{1-10}$ alkylene;

R$^2$ is selected from H, C$_{1-5}$ alkylene-Q', (CH$_2$)$_r$O(CH$_2$)$_r$—Q', (CH$_2$)$_r$NR$^a$(CH$_2$)$_r$—Q', (CRR')$_r$NR$^a$C(O)(CRR')$_r$—Q', (CH$_2$)$_r$C(O)NR$^a$(CH$_2$)$_r$—Q', (CRR')$_r$NR$^a$C(O)NR$^a$(CRR')$_r$—Q', and (CH$_2$)$_r$C(O)(CH$_2$)$_r$—Q';

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–9 membered heterocyclic system containing from 1–4 heteroatoms selected from the group consisting of N, O, and S; and, Q is selected from H, a C$_{5-6}$ carbocycle substituted with 0–5 R$^b$ and a 5–6 membered heterocyclic system containing from 1–4 heteroatoms selected from the group consisting of N, O, and S and substituted with 0–5 R$^b$.

4. A compound according to claim 3, wherein;

A is selected from —CONHOH and —N(OH)CHO;

X$^a$ is absent or C$_{1-4}$ alkylene;

Y$^a$ is absent or selected from O and NR$^a$;

Z$^a$ is selected from H, a C$_{5-10}$ carbocycle substituted with 0–5 R$^c$ and a 5–10 membered heterocyclic system containing from 1–4 heteroatoms selected from the group consisting of N, O, and S and substituted with 0–5 R$^c$;

R$^4$ is selected from H, C$_{1-4}$ alkylene-H, (CH$_2$)$_r$O(CH$_2$)$_r$—H, and (CH$_2$)$_r$NR$^a$(CH$_2$)$_r$—H; and, R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^a$, CF$_3$, CF$_2$CF$_3$, and a 5–6 membered heterocyclic system containing from 1–4 heteroatoms selected from the group consisting of N, O, and S.

5. A compound according to claim 1, wherein the compound is selected from:

(αS,3R)-α-[(2,2-dimethyl-1-oxopropyl)amino]-N-hydroxy-1-[4-[(2-methyl-4-quinolinyl)methoxy]phenyl]-2-oxo-3-pyrrolidineacetamide;

1,1-dimethylethyl [2-(hydroxyamino)-(1S)-1-[1-[4-[(2-methyl-4-quinolinyl)methoxy]phenyl]-2-oxo-(3R)-3-pyrrolidinyl]-2-oxoethyl]carbamate;

(αS,3R)-α-amino-N-hydroxy-1-[4-[(2-methyl-4-quinolinyl)methoxy]phenyl]-2-oxo-3-pyrrolidineacetamide;

(αS,3R)-α-(acetylamino)-N-hydroxy-1-[4-[(2-methyl-4-quinolinyl)methoxy]phenyl]-2-oxo-3-pyrrolidineacetamide;

N-[2-(hydroxyamino)-(1S)-1-[1-[4-[(2-methyl-4-quinolinyl)methoxy]phenyl]-2-oxo-(3R)-3-pyrrolidinyl]-2-oxoethyl]-4-morpholinecarboxamide;

1,1-dimethylethyl [(1S)-1-[1-[4-[(2,6-dimethyl-4-pyridinyl)methoxy]phenyl]-2-oxo-(3R)-3-pyrrolidinyl]-2-(hydroxyamino)-2-oxoethyl]carbamate;

(αS,3R)-α-amino-1-[4-[(2,6-dimethyl-4-pyridinyl)methoxy]phenyl]-N-hydroxy-2-oxo-3-pyrrolidineacetamide;

methyl (1S)-2-(hydroxyamino)-1-((3R)-1-{4-[(2-methyl-4-quinolinyl)methoxy]phenyl}-2-oxopyrrolidinyl)-2-oxoethylcarbamate;

butyl (1S)-2-(hydroxyamino)-1-((3R)-1-{4-[(2-methyl-4-quinolinyl)methoxy]phenyl}-2-oxopyrrolidinyl)-2-oxoethylcarbamate;

N-[(1S)-2-(hydroxyamino)-1-((3R)-1-{4-[(2-methyl-4-quinolinyl)methoxy]phenyl}-2-oxopyrrolidinyl)-2-oxoethyl]benzamide;

(2S)-N-hydroxy-2-((3R)-1-{4-[(2-methyl-4-quinolinyl)methoxy]phenyl}-2-oxopyrrolidinyl)-2-(1H-pyrrol-1-yl)ethanamide;

(2S)-2-(dimethylamino)-N-hydroxy-2-((3R)-1-{4-[(2-methyl-4-quinolinyl)methoxy]phenyl}-2-oxopyrrolidinyl)ethanamide;

(2R)-N-hydroxy-2-((3R)-1-{4-[(2-methyl-4-quinolinyl)methoxy]phenyl}-2-oxopyrrolidinyl)propanamide;

(2S)-N-hydroxy-2-((3R)-1-{4-[(2-methyl-4-quinolinyl)methoxy]phenyl}-2-oxopyrrolidinyl)propanamide;

(2R)-N-hydroxy-2-((3R)-1-{4-[(2-methyl-4-quinolinyl) methoxy]phenyl}-2-oxopyrrolidinyl)pentanamide;

(2S)-N,2-dihydroxy-2-((3R)-1-{4-[(2-methyl-4-quinolinyl)methoxy]phenyl}-2-oxopyrrolidinyl) ethanamide;

(1S)-1-{(3R)-1-[4-(benzyloxy)phenyl]-2-oxopyrrolidinyl}ethyl(hydroxy)formamide;

hydroxy[(1S)-1-((3R)-1-{4-[(2-methyl-4-quinolinyl) methoxy]phenyl}-2-oxopyrrolidinyl)ethyl]formamide;

(2R,S)-((3S,R)-3-amino-1-{4-[2-methyl-4-quinolinyl) methoxy]phenyl}-2-oxopyrrolidinyl)-N-hydroxypentanamide;

(2SR)-((3S,R)-3-amino-1-{4-[2-methyl-4-quinolinyl) methoxy]phenyl}-2-oxopyrrolidinyl)-N-hydroxypentanamide;

(2S,R)-((3S,R)-3-amino-1-{4-[2-methyl-4-quinolinyl) methoxy]phenyl}-2-oxopyrrolidinyl)-N-hydroxypropanamide;

(2S,R)-((3S,R)-3-(dimethylamino)-1-1 4-[2-methyl-4-quinolinyl)methoxy]phenyl}-2-oxopyrrolidinyl)-N-hydroxypropanamide; and, 2-((3S,R)-3-amino-1-{4-[2-methyl-4-quinolinyl) methoxy]phenyl}-2-oxopyrrolidinyl hydroxyacetamide;

or a pharmaceutically acceptable salt form thereof.

6. A pharmaceutical composition, comprising: a pharmaceutically acceptable carrier and a therapeutically effective amount of a compound of claim 1 or a pharmaceutically acceptable salt form thereof.

7. A pharmaceutical composition, comprising: a pharmaceutically acceptable carrier and a therapeutically effective amount of a compound of claim 2 or a pharmaceutically acceptable salt form thereof.

8. A pharmaceutical composition, comprising: a pharmaceutically acceptable carrier and a therapeutically effective amount of a compound of claim 3 or a pharmaceutically acceptable salt form thereof.

9. A pharmaceutical composition, comprising: a pharmaceutically acceptable carrier and a therapeutically effective amount of a compound of claim 4 or a pharmaceutically acceptable salt form thereof.

10. A pharmaceutical composition, comprising: a pharmaceutically acceptable carrier and a therapeutically effective amount of a compound of claim 5 or a pharmaceutically acceptable salt form thereof.

11. A method for treating an inflammatory disorder, comprising: administering to a patient in need thereof a therapeutically effective amount of a compound of claim 1 or a pharmaceutically acceptable salt form thereof.

12. A method for treating an inflammatory disorder, comprising: administering to a patient in need thereof a therapeutically effective amount of a compound of claim 2 or a pharmaceutically acceptable salt form thereof.

13. A method for treating an inflammatory disorder, comprising: administering to a patient in need thereof a therapeutically effective amount of a compound of claim 3 or a pharmaceutically acceptable salt form thereof.

14. A method for treating an inflammatory disorder, comprising: administering to a patient in need thereof a therapeutically effective amount of a compound of claim 4 or a pharmaceutically acceptable salt form thereof.

15. A method for treating an inflammatory disorder, comprising: administering to a patient in need thereof a therapeutically effective amount of a compound of claim 5 or a pharmaceutically acceptable salt form thereof.

16. A method of treating a condition or disease wherein the disease or condition is selected from rheumatoid arthritis, osteoarthritis, periodontitis, gingivitis, corneal ulceration, neovascular glaucoma, multiple sclerosis, psoriasis, fever, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 1 or a pharmaceutically acceptable salt form thereof.

17. A method of treating a condition or disease wherein the disease or condition is selected from rheumatoid arthritis, osteoarthritis, periodontitis, gingivitis, corneal ulceration, neovascular glaucoma, multiple sclerosis, psoriasis, fever, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 2 or a pharmaceutically acceptable salt form thereof.

18. A method of treating a condition or disease wherein the disease or condition is selected from rheumatoid arthritis, osteoarthritis, periodontitis, gingivitis, corneal ulceration, neovascular glaucoma, multiple sclerosis, psoriasis, fever, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 3 or a pharmaceutically acceptable salt form thereof.

19. A method of treating a condition or disease wherein the disease or condition is selected from rheumatoid arthritis, osteoarthritis, periodontitis, gingivitis, corneal ulceration, neovascular glaucoma, multiple sclerosis, psoriasis, fever, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 4 or a pharmaceutically acceptable salt form thereof.

20. A method of treating a condition or disease wherein the disease or condition is selected from rheumatoid arthritis, osteoarthritis, periodontitis, gingivitis, corneal ulceration, neovascular glaucoma, multiple sclerosis, psoriasis, fever, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of claim 5 or a pharmaceutically acceptable salt form thereof.

* * * * *